(12) United States Patent
Gonzaga-Jauregui et al.

(10) Patent No.: US 10,463,029 B1
(45) Date of Patent: Nov. 5, 2019

(54) RODENT MODEL OF STEEL SYNDROME

(71) Applicant: Regeneron Pharmaceuticals, Inc., Tarrytown, NY (US)

(72) Inventors: Claudia Gonzaga-Jauregui, Elmsford, NY (US); Chia-Jen Siao, New York, NY (US); Harikiran Nistala, Tarrytown, NY (US); Kalyan C. Nannuru, Yorktown Heights, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 16/002,233

(22) Filed: Jun. 7, 2018

(51) Int. Cl.
*A01K 67/027* (2006.01)
*A61K 49/00* (2006.01)
*C07K 14/78* (2006.01)

(52) U.S. Cl.
CPC ...... *A01K 67/0275* (2013.01); *A61K 49/0008* (2013.01); *C07K 14/78* (2013.01); *A01K 2217/07* (2013.01); *A01K 2227/105* (2013.01); *A01K 2267/0306* (2013.01)

(58) Field of Classification Search
CPC .......... A01K 67/0275; A01K 2227/105; A01K 2267/0306; A01K 2217/07; A61K 49/008; C07K 14/78
USPC ................................................. 800/18, 3, 21
See application file for complete search history.

(56) References Cited

U.S. PATENT DOCUMENTS

| | | | |
|---|---|---|---|
| 7,294,754 | B2 | 11/2007 | Poueymirou et al. |
| 7,576,259 | B2 | 8/2009 | Poueymirou et al. |
| 7,659,442 | B2 | 2/2010 | Poueymirou et al. |
| 2008/0078000 | A1 | 3/2008 | Poueymirou et al. |
| 2014/0235933 | A1 | 8/2014 | Lee et al. |
| 2014/0310828 | A1 | 10/2014 | Lee et al. |

OTHER PUBLICATIONS

Plumb et al. (2011) PLoS ONE, vol. 6(12), e29422, pp. 1-12.*
Tong et al. (2010) Nature, vol. 467(7312), 211-213.*
Munoz et al. (2009) Stem Cell Rev. and Rep., vol. 5, 6-9.*
Prelle et al. (2002) Anat. Histol. Embryol., vol. 31, 169-186.*
Wheeler (2001) Theriogenology. vol. 56, 1345-1369.*
Niemann et al (2005) Rev. Sci, Tech. Off. Int. Spiz. vol. (24), 285-298.*
Clark et al. (2003) Nature Reviews: Genetics. vol. 4, 825-833.*
Gonzaga-Jauregui et al. (2015) Eur. J. Hum. Genet., ol. 23, 342-346.*
Mullins et al. (1996) J. Clin. Invest., vol. 98(11), S37-S40.*
Dave et al. (2014) Neurobiol. Dis., vol. 70, 190-203.*
Belbin G M. et al., "Genetic Identification of a Common Collagen Disease in Puerto Ricans Via Identity-By-Descent Mapping in a Health System", eLIFE 6:e25060 (2017).
Boot-Handford R.P. et al., "A Novel and Highly Conserved Collagen (proα1 (XXVII)) With a Unique Expression Pattern and Unusual Molecular Characteristics Establishes a New Clade Within the Vertebrate Fibrillar Collagen Family", The Journal of Biological Chemistry 278(33):31067-31077 (Aug. 15, 2003).
Christiansen H.E. et al., "Critical Early Roles for col27a1a and col21a1b in Zebrafish Notochord Morphogenesis, Vertebral Mineralization and Post-Embryonic Axial Growth", PLoS One 4(12):e8481 (Dec. 2009).
Das N M et al., "In Vivo Quantitative Microcomputed Tomographic Analysis of Vasculature and Organs in a Normal and Diseased Mouse Model", PLoS One 11(2):e0150065 ( Feb. 24, 2016).
Gariballa N. et al., "A Novel Aberrant Splice Site Mutation in COL27A1 is Responsible for Steel Syndrome and Extension of the Phenotype to Include Hearing Loss", American Journal of Medical Genetics 173A:1257-1263 (2017).
Gonzaga-Jauregui C. et al., "Mutations in COL27A1 Cause Steel Syndrome and Suggest a Founder Mutation Effect in the Puerto Rican Population", European Journal of Human Genetics 23:342-346 (2015).
Hjorten R. et al., "Type XXVII Collagen at the Transition of Cartilage to Bone During Skeletogenesis", Bone 41:535-542 (2007).
Kotabagi S. et al., "Second Family Provides Further Evidences for Causation of Steel Syndrome by Biallelic Mutations in COL27A1", Clin Gent. 92(3):323-326 (Sep. 2017).
Pace J M. et al., "Identification, Characterization and Expression Analysis of a New Fibrillar Collagen Gene, COL27A1", Matrix Biology 22:3-14 (2003).
Plumb D.A. et al., "Collagen XXVII Organises the Pericellular Matrix in the Growth Plate", PLoS ONE 6(12):e29422 (Dec. 2011).
Plumb D.A. et al., "Collagen XXVII is Developmentally Regulated and Forms Thin Fibrillar Structures Distinct from Those of Classical Vertebrate Fibrillar Collagens", The Journal of Biological Chemistry 282(17):12791-12795 (Apr. 27, 2007).
Poueymirou T. et al., "F0 Generation Mice Fully Derived from Gene-Targeted Embryonic Stem Cells Allowing Immediate Phenotypic Analyses", Nature Biotechnology 25(1):91-99 (Jan. 2007).
Steel H.H. et al., "A Syndrome of Dislocated Hips and Radial Heads, Carpal Coalition, and Short Stature in Puerto Rican Children", The Journal of Bone and Joint Surgery 75-A(2):259-264 (Feb. 1993).
Valenzuela D.M. et al., "High-Throughput Engineering of the Mouse Genome Coupled With High-Resolution Expression Analysis", Nature Biotechnology 21(6):652-659 (Jun. 2003).
NCBI Reference Sequence No. NP_942042.1 (4 pages) (May 27, 2018).
NCBI Reference Sequence No. NP_116277.2 (6 pages) (Jun. 30, 2018).
NCBI Reference Sequence No. NP_079961.3 (5 pages) (Jun. 23, 2018).

(Continued)

*Primary Examiner* — Anne Marie S Wehbe
(74) *Attorney, Agent, or Firm* — Scully, Scott, Murphy & Presser, P.C.; Brian A. Cocca

(57) ABSTRACT

This disclosure relates to a rodent model of Steel Syndrome. Disclosed herein are genetically modified rodent animals that carry a mutation in an endogenous rodent Col27a1 gene, equivalent to a mutation in humans causing Steel Syndrome.

13 Claims, 9 Drawing Sheets
(6 of 9 Drawing Sheet(s) Filed in Color)
Specification includes a Sequence Listing.

(56) References Cited

OTHER PUBLICATIONS

NCBI Reference Sequence No. NM_198747.1 (8 pages) (May 27, 2018).
NCBI Reference Sequence No. NM_032888.3 (13 pages) (Jun. 30, 2018).
NCBI Reference Sequence No. NM_025685.3 (11 pages) (Jun. 23, 2018).

* cited by examiner

```
COL27A1 Protein alignment (Hsapiens - Mmusculus - Rnorvegicus)

....|....| ....|....| ....|....| ....|....| ....|....| ....|....| ....|....|
                            10         20         30         40         50         60         70
Mmusculus_          ----------M GTGFAPGARG TAASGPGGGF LFAWILVSFT CKLASTQGAP EDVDVLQRLG LSWTKAGGGR
Rnorvegicu          MGLARATAGL GPCCPPAPAL LGAGLRWGGF LFAWILVSFS CKLASTQGAP EDVDVLQRPLG LSWTKAGGGP
Hsapiens_N          -------MGA GSARGARGTA AAAAARGGGF LFSWILVSFA CHLASTQGAP EDVDILQRLG LSWTKAG---
Clustal Co                  *.        .*.   *** **:******: ********** ****:***** *******

....|....| ....|....| ....|....| ....|....| ....|....| ....|....| ....|....|
                            80         90        100        110        120        130        140
Mmusculus_          SPTPPGVIPF PSGFIFTQRA KLQAPTANVL PTTLGRELAL VLSLCSHRVN HAFLFAIRSR KHKLQLGLQF
Rnorvegicu          SPAPPGVIPF PSGFIFTQRA KLQAPTTNVL PTTLGRELAL VLSLCSHRVN HAFLFAIRSR KHPLQLGLQF
Hsapiens_N          SPAPPGVIPF QSGFIFTQRA RLQAPTGTVI PAALGTELAL VLSLCSHRVN HAFLFAVRSQ KRKLQLGLQF
Clustal Co          **:******* ********* :***** ,*: *::** **** ********** ******:**: *::*******

....|....| ....|....| ....|....| ....|....| ....|....| ....|....| ....|....|
                           150        160        170        180        190        200        210
Mmusculus_          LPGRTIIHLG PRQSVAFDLD VHDGRWHHLA LELRGRTVTM VTACGQHRVP VPLPSRRDSM LDPQGSFLLG
Rnorvegicu          LPGRTLVHLG PRQSVAFDLD VHDGRWHHLA LELRGRTVTL VTACGQHRVP VPLPSRRDSM LDPQGSFLLG
Hsapiens_N          LPGKTVVHLG SPRSVAFDLD MHDGRWHHLA LELRGRTVTL VTACGQRPVP VLLPFHRDPA LDPGGSFLFG
Clustal Co          ***:*::*** ,*:******* :********* ********** :*******:*** * ** :**.  *** ****:*

....|....| ....|....| ....|....| ....|....| ....|....| ....|....| ....|....|
                           220        230        240        250        260        270        280
Mmusculus_          KVNPRAVQFE GALCQFSIBF VAQVAHNYCA HLREPCRQVD TYSPQVGTLF PWDSGPAFAL HPEPALLGLG
Rnorvegicu          KMNPRAVQFE GALCQFSIBF VAQVAHNYCA HLREPCRQVD TYGPQVGALF PWDSGPAFAL HPEPALLGLG
Hsapiens_N          KMMPHAVQFE GALCQFSIYP VTQVAHNYCT HLRKQCGQAD TYQSPLGFLF SQDSGRPFTF QSDLALLGLE
Clustal Co          *:**:***** ********:* *:*******: ***:: *.* ** . :*.** . *** .*:: :.: *****

....|....| ....|....| ....|....| ....|....| ....|....| ....|....| ....|....|
                           290        300        310        320        330        340        350
Mmusculus_          NLTRTPATLG AREVSRALAV TLAPAMPTKP LR------TVHP DVSEHSSSQT PLSPAKQSAR KTPSPSSSAS
Rnorvegicu          NLTRNPATLG SRPISRGLMV TMAPAVPTKP LR------MVHQ DVSKLGSSQT PLVPAKQSAR KTPSPFPSAA
Hsapiens_N          NLTTATPALS SLPAGRGPRG TVAPATPTKP QRTSPTNPHQ HMAVGGPAQT PLLPAKLSAS NALDPMLPAS
Clustal Co          ***  ..::** : * .*.  *:*** ****    *        * .:: ..:** ** *** ** :: .*  .*:

....|....| ....|....| ....|....| ....|....| ....|....| ....|....| ....|....|
                           360        370        380        390        400        410        420
Mmusculus_          LANSTPVYRP AAAQPRQ--IT TTSPTKRSPT KPSVSPLSVT PMKSPHATQK TGVPSFTKPV PPTQKPAPFT
Rnorvegicu          LANSTPVFHS APAQPRQ--IT ATSPTKRPPT KPSVSSLSVT PMKSPQAIQK AGTPSFSRPI PTTQKPTPLT
Hsapiens_N          VGGSTRTPRP AAAQPSQKIT ATKIPKSLPT KPSAPSTSIV FIKSPHPTQK TAPSSFTKSA LPTQKQVPPT
Clustal Co          :..***.  :. *:*** * ** :*.  .*  ** ***..,. *:.  *:****:. ** ::  .**::.   .*** .* *

....|....| ....|....| ....|....| ....|....| ....|....| ....|....| ....|....|
                           430        440        450        460        470        480        490
Mmusculus_          SYLAPSKASS PTVRPVQKTF MTPRPPVPSP QPLRPTTGLS KKFTNPTVAK SESKTTSWAS KPVLARSSVP
Rnorvegicu          SRPSPSKVSS ATVRPVQKTF MTPQPPTLSP QALRPITGLP KKFTIPTVAK PQSKMTSWAS KPVLARTNVP
Hsapiens_N          SRPVPARVSR PAEKPIQRNP GMPRPPPPST RPLPPTTSS- SKKPIPTLAR TEAKITSHAS KPASARTSTH
Clustal Co          *  *::.*  .: :*:*:,.    *:**  *,.* *.,    .* . **:*: ..:* ** ** **. **:..

....|....| ....|....| ....|....| ....|....| ....|....| ....|....| ....|....|
                           500        510        520        530        540        550        560
Mmusculus_          PTLQQTVLSG SPVSYLG--- --SQTLAPAL PPLGVGNPRT MPPTRDSALT PAGSKKFTGR ETSKKTRQKS
Rnorvegicu          KALEQTVVAQ SSVSYLG--- --SQTLATAL PPLGVGNSRM MPSTRDSTST PAGSKKKITGL EASFKTRHFS
Hsapiens_N          KPPPFTALSS SPAPTPGSTR STRPPATMVP PTSGTSTPRT APAVPTPGSA PTGSKKPIGS EASKKAGPKS
Clustal Co          *.  *.::.. *...  *    .  . *. *..  ..  * ; *:****  *  *:***: **
```

FIG. 5A

```
                     ....|....|  ....|....|  ....|....|  ....|....|  ....|....|  ....|....|  ....|....|
                         570         580         590         600         610         620         630
Mmusculus_     SPRKPEPLSP  GKSARDASPR  DLTTKPS---  -----PPSTPA  LVLAPAYLLS  SSPQPTSSSF  PFFHLLGPTP
Rnorvegicu     SPRKPIPLSS  GKTARDASPR  DLTTKPS---  -----QLSTPA  LVLAPAHLLS  SSPQPTSSSF  SFFHLPEPTP
Hsapiens_N     SPRKPVPLRP  GKAARDVPLS  DLTTRPSPRQ  PQPSQQTTPA  LVLAPAQFLS  SSPRPTSSGY  STFHLAGSTP
Clustal Co     *****  **  .  **:***..   ****;**              ; ;***  ******  ;**  ***;****.;  .;***  .**

....|....|  ....|....|  ....|....|  ....|....|  ....|....|  ....|....|  ....|....|
                         640         650         660         670         680         690         700
Mmusculus_     PPMLMGPPGS  KGDCGLPGPP  GLPGLPGSPG  ARGPRGPPGP  YGNPGPPGPP  GAKGQKGDPG  LSPGQAHDGA
Rnorvegicu     PLMLMGPPGS  KGDCGLPGPP  GLPGLPGSPG  PRGPRGPPGP  FGNPGLPGPP  GAKGQKGDPG  LSPGQAHDGA
Hsapiens_N     PPLLMGPPGP  KGDCGLPGPP  GLPGLPGIPG  ARGPRGPPGP  YGNPGLPGPP  GAKGQKGDPG  LSPGKAHDGA
Clustal Co     *.;*****.   **********  ******  **  .*********  ;****  ****  **********  ****;*****

....|....|  ....|....|  ....|....|  ....|....|  ....|....|  ....|....|  ....|....|
                         710         720         730         740         750         760         770
Mmusculus_     KGNMGLP LS  GNPGPLGRKG  HKGHPGAAGH  PGEQGQPGPE  GSPGAKGYPG  RQGFPGPVGD  PGPKGSRGYI
Rnorvegicu     KGNMGLP LA  GNPGPMGRKG  HKGHPGAAGH  PGEQGQPGPE  GSPGAKGYPG  RQGFPGPVGD  PGPKGSRGYI
Hsapiens_N     KGDMGLP LS  GNPGPPGRKG  HKGYPGPAGH  PSEQGQPGPE  GSPGAKGYPG  RQGLPGPVGD  PGPKGSRGYI
Clustal Co     **;******;  *****  ****  ***;**.***  **********  **********  ***;******  **********

....|....|  ....|....|  ....|....|  ....|....|  ....|....|  ....|....|  ....|....|
                         780         790         800         810         820         830         840
Mmusculus_     GLPGLPGLPG  SDGERGLPGV  PGKRGEMGRP  GFPGDFGERG  PPGLDGNPGE  IGLPGPPGVL  GLIGDTGALG
Rnorvegicu     GLPGLPGLPG  SDGERGLPGI  PGKRGEMGRP  GFPGDFGERG  PPGLDGNPGE  IGLPGPPGVL  GLLGDMGALG
Hsapiens_N     GLPGLPGLPG  SDGERGLPGV  PGKRGKMGMP  GFPGVFGERG  PPGLDGNPGE  LGLPGPPGVP  GLIGDLGVLG
Clustal Co     **********  **********;  ****;**  *   ****  *****  **********  ;*********  **;**  *.**

....|....|  ....|....|  ....|....|  ....|....|  ....|....|  ....|....|  ....|....|
                         850         860         870         880         890         900         910
Mmusculus_     PVGYPGPKGM  KGLMGGVGEP  GLKGDKGEQG  VPGVSGDPGF  QGDKGSHGLP  GLPGGRGKPG  PLGKAGDKGS
Rnorvegicu     PVGYPGPKGM  KGLMGGVGEP  GLKGDKGEQG  VPGVSGDPGF  QGDKGSHGLP  GFPGARGKPG  PMGKAGDKGS
Hsapiens_N     PIGYPGPKGM  KGLMGSVGEP  GLKGDKGEQG  VPGVSGDPGF  QGDKGSQGLP  GFPGARGKPG  PLGKVGDKGS
Clustal Co     *;********  ****;****   **********  **********  ******;***  *;**.*****  *;**.*****

....|....|  ....|....|  ....|....|  ....|....|  ....|....|  ....|....|  ....|....|
                         920         930         940         950         960         970         980
Mmusculus_     LGFPGPPGPE  GFPGDIGPPG  DNGPEGMKGK  PGARGLPGPP  GQLGPEGDEG  PMGPPGVPGL  EGQPGRKGFP
Rnorvegicu     LGLPGPPGPE  GFPGDIGPPG  DNGPEGMKGK  PGARGLPGPP  GQLGPEGDEG  PMGPPGVPGL  EGQPGPKGFP
Hsapiens_N     IGFPGPPGPE  GFPGDIGPPG  DNGPEGMKGK  PGARGLPGPR  GQLGPEGDEG  PMGPPGAPGL  EGQPGRFGFP
Clustal Co     ;*;*******  **********  **********  *********   **********  ******.***  *********

....|....|  ....|....|  ....|....|  ....|....|  ....|....|  ....|....|  ....|....|
                         990        1000        1010        1020        1030        1040        1050
Mmusculus_     GRPGLDGSKG  EPGDPGPPGP  VGEQGLMGFI  GLVGEPGIVG  EKGDRGVMGP  PGAPGPPKGSM  GHPGTPGGIG
Rnorvegicu     GFPGLDGVKG  EPGDPGRPGP  VGEQGFMGPI  GLVGEPGIVG  EKGDRGMMGP  PGVPGPPKGSM  GHPGMPGGMG
Hsapiens_N     GRPGLDGVKG  EPGDPGRPGP  VGEQGFMGPI  GLVGEPGIVG  EKGDRGMMGP  PGVPGPFKGSM  GHPGMPGGMG
Clustal Co     ******..**  **********  ******;***;  **********  *****;***  **.*******  ****  ***;*

....|....|  ....|....|  ....|....|  ....|....|  ....|....|  ....|....|  ....|....|
                        1060        1070        1080        1090        1100        1110        1120
Mmusculus_     NPGEPGPWGP  PGSRGLPGMR  GAKGHRGPRG  PDGPAGEQGS  KGLKGRVGPR  GRPGQPGQQG  AAGERGHSGA
Rnorvegicu     DPGEPGPWGP  PGSRGLPGMR  GAKGHRGPRG  PDGPAGEQGS  RGLKGRVGPR  GRPGQPGQQG  AAGERGHSGA
Hsapiens_N     TPGEPGPQGP  PGSRGPPGMR  GAKGHRGPRG  PDGPAGEQGS  RGLKGPPGPD  GRPGHPGQQG  VAGERGHLGS
Clustal Co     ******.**   *****.****  **********  **********  ;****  **;   **;*****  .*****.*;
```

FIG. 5B

```
                    1130       1140       1150       1160       1170       1180       1190
Mmusculus_    KGFLGIPGPS GPPGAKGLPG EPGSQGPQGP VGPPGEMGPK GPPGAVGEPG LPGDSGMKGD LGPLGPPGEQ
Rnorvegicu    KGFLGIPGPS GPPGAKGLPG EPGSQGPQGP VGPPGEMGPK GPPGAVGEPG LPGDSGMKGD LGPLGPPGEQ
Hsapiens_N    RGFPGIPGPS GPPGTKGLPG EPGPQGPQGP IGPPGEMGPK GPPGAVGEPG LPGEAGMKGD LGPLGTPGEQ
Clustal Co    :** ****** ****:***** ***.****** ,********* ********** ***:;***** *****.****

1200       1210       1220       1230       1240       1250       1260
Mmusculus_    GLIGQRGEPG LEGDHGPVGP DGLKGDRGDP GPDGEHGEKG QEGLKGEDGS PGPPGITGVP GREGKPGKQG
Rnorvegicu    GLIGQRGEPG LEGDLGPVGP DGLKGDRGDP GPDGEHGEKG QEGLKGEEGL PGPPGITGVR GPEGKFGSQG
Hsapiens_N    GLIGQRGEPG LEGDSGPMGP DGLKGDRGDP GPDGEHGEKG QEGLMGEDGP PGPPGVTGVR GPEGKSGKQG
Clustal Co    ********** ****.**;** ********** ********** ****.**;*. *****;*** . ***.*..**

1270       1280       1290       1300       1310       1320       1330
Mmusculus_    EKGQRGAKGA KGHQGYLGEM GIPGEPGPPG TPGPKGSRGT LGPTGAPGRM GAQGEPGLAG YNGHKGITGP
Rnorvegicu    EKGQRGAKGA KGYQGQLGEM GIPGDPGPPG TPGPKGSRGT LGPMGAPGRM GAQGEPGLAG YNGHKGITGP
Hsapiens_N    EKGRTGAKGA KGYQGQLGEM GVPGDPGPPG TPGPKGSRGS LGPTGAPGRM GAQGEPGLAG YDGHKGIVGP
Clustal Co    ***: ***** **;** **** *;**;***** **********; *** ****** ********** *;*****.**

1340       1350       1360       1370       1380       1390       1400
Mmusculus_    LGPPGPKGEK GDQGEDGKTE GPPGPPGDRG PVGDRGDRGE PGDPGYPGQE GVQGSLRGEPG QQGQPGHPGP
Rnorvegicu    LGPPGPKGEK GEQGEDGKTE GAPGPPGERG PVGDRGDRGE PGDPGYPGQE GVQGSLRGEPG QQGQPGHPGP
Hsapiens_N    LGPPGPKGEK GEQGEDGKAE GPPGPPGDRG PVGDRGDRGE PGDPGYPGQE GVQGSLRGPG QQGQPGHPGP
Clustal Co    ********** *;:*****;* *.*****;** ********** ********** *******;** **********

1410       1420       1430       1440       1450       1460       1470
Mmusculus_    RGRPGPKGSK GEEGPKGKEG KAGPSGRRGT QGLQGLPGPR GVVGRQGPEG TAGSDGIPGR DGPPGYQGDQ
Rnorvegicu    RGRPGPKGSK GEEGPKGKPG KAGASGRRGT QGLQGLPGPR GVVGRQGPEG MAGQDGNPGR DGPPGYQGEQ
Hsapiens_N    RGWPGPKGSK GAEGPKGKQG KAGAPGRRGV QGLQGLPGPR GVVGRQGLEG IAGPDGLPGR DGQAGQQGEQ
Clustal Co    ** ******* * ****** * ***,.****. ********** ****** ** ** **.*** **;.* **;*

1480       1490       1500       1510       1520       1530       1540
Mmusculus_    GNDGDPGPVG PAGRRGNPGV AGLPGAQGPP GFKGESGLPG QLGPPGKRGT EGGTGLPGNQ GEPGSKGQPG
Rnorvegicu    GNDGDPGPVG PAGRRGNPGV AGLPGAQGPP GFKGESGLPG QLGPPGKRGT EGGTGLPGNQ GEPGSKGQPG
Hsapiens_N    GDDGDPGPMG PAGKRGNPGV AGLPGAQGPP GFKGESGLPG QLGPPGKRGT EGRTGLPGNQ GEPGSKGQPG
Clustal Co    *;******;* ***;****** ********** ********** ********** ** ******* **********

1550       1560       1570       1580       1590       1600       1610
Mmusculus_    DSGEMGFPGV AGLFGFKGPP GDIGFKGIQG PRGPPGLMGK EGIIGPPGML GPSGLPGPKG DRGSRGDLGL
Rnorvegicu    DSGEMGFPGV AGLFGPKGPP GDIGFKGIQG PRGPPGLMGK EGIIGPPGML GPSGLPGPKG DRGSRGDWGL
Hsapiens_N    DSGEMGFPGM AGLFGPKGPP GDIGFKGIQG PRGPPGLMGK EGIVGPLGIL GPSGLPGPKG DKGSRGDWGL
Clustal Co    ********:; ***;****** ********** ********** ***;.** *;* ********** *;**** **

1620       1630       1640       1650       1660       1670       1680
Mmusculus_    QGPKGPPGPR GPPGPPGPPW HPIQFQQDDL GAAFQTWMPA QGAVRSEG-Y SYPDQLALDQ GGEIFKTLHY
Rnorvegicu    QGPKGPPGPR GPPGPPGPPW HPVQFQQDDL EAAFQTWMDA BGAVPLEQGY SYPDQLMLDQ GGEIFKTLHY
Hsapiens_N    QGPKGPPGPR GPPGPPGPPG GPIQLQQDDL GAAFQTWMDT SGALFPES-Y SYPDRLVLDQ GGEIFKTLHY
Clustal Co    ********** **********   *;;***** ********: **;* * * ****;* *** **********

1690       1700       1710       1720       1730       1740       1750
Mmusculus_    LSNLIQSIKT PLGTKENPAR VCRDLMDCEQ RMADGTYWVD PHLGCSSDTI EVSCNFTQGG QTCLKPITAS
```

FIG. 5C

```
Rnorvegicu  LSNLIQSIKT PLGTKENPAR VCRDLMDCEQ KMADGIYWVD PNLGCSSDTI EVSCNFTHGG QTCLKPITAS
Hsapiens_N  LSNLIQSIKT PLGTKENPAR VCRDLMDCEQ KMVDGTYWVD PNLGCSSDTI EVSCNFTHGG QTCLKPITAS
Clustal Co  ********** ********** ********** :*.** **** ********** *******:** **********

....|....| ....|....| ....|....| ....|....| ....|....| ....|....| ....|....|
                   1760       1770       1780       1790       1800       1810       1820
Mmusculus_  KAEFAVSRVQ MNFLHLLSSE GTQHITIHCL NMTVWQEGPG PSSARQAVRF RAWNGQVFEA GGQFRPEVSM
Rnorvegicu  KAEFAVSPVQ MNFLHLLSSE GTQHITIHCL NMTVWQEGPA KPSARQAVRF RAWNGQVFEA GGQFPPEVSM
Hsapiens_N  KVEFAISPVQ MNFLHLLSSE VTQHITIHCL NMTVWQEGTG QTPAKQAVRF RAWNGQIFEA GGQFPPEVSM
Clustal Co  *.***:**** ********** .********* ********,, :..*:***** *****:*** *********

....|....| ....|....| ....|....| ....|....| ....|....| ..
                   1830       1840       1850       1860       1870
Mmusculus_  DGCKVEDGRW HQTLFTPRTQ DPQQLPIVSV DNLPPVSSGK QYRLEVGPAC FL (SEQ ID NO: 4)
Rnorvegicu  DGCKVEDGRW HQTLFTFRTQ DPQQLPIVSV DNLPPVSSGK QYRLEVGPAC FL (SEQ ID NO: 6)
Hsapiens_N  DGCKVQDGRW HQTLFTFRTQ DPQQLPIISV DNLPPASSGK QYRLEVGPAC FL (SEQ ID NO: 2)
Clustal Co  *****:**** ********** *******:** *****,**** ********** **
```

RODENT MODEL OF STEEL SYNDROME

FIELD OF THE DISCLOSURE

This disclosure relates to an animal model of human disease. More specifically, this disclosure relates to a rodent model of Steel Syndrome. Disclosed herein are genetically modified rodent animals that carry a mutation in an endogenous rodent Col27a1 gene, equivalent to a mutation in humans causing Steel Syndrome, and that recapitulate features observed in humans having Steel Syndrome.

INCORPORATION BY REFERENCE OF SEQUENCE LISTING

The sequence listing in the ASCII text file, named as 10433US01_35992_SequenceListing of 75 KB, created on May 14, 2018, and submitted to the United States Patent and Trademark Office via EFS-Web, is incorporated herein by reference.

BACKGROUND ART

Various publications, including patents, patent applications, published patent applications, accession numbers, technical articles and scholarly articles are cited throughout the specification. Each of these cited publications is incorporated by reference, in its entirety and for all purposes, in this document.

Steel Syndrome (MIM #615155) was first described by Steel et al. in 1993 as an orthopedic syndrome observed in 23 Hispanic children from Puerto Rico (Steel et al., J. Bone Joint Surg. Am. 75: 259-264, 1993). The main clinical features include congenital bilateral hip and radial head dislocation, short stature, carpal coalitions, scoliosis, foot abnormalities, and mildly dysmorphic features.

Clinical and genetic evaluation of patients with STLS pointed to a distinct genetic syndrome different from other well-characterized skeletal dysplasias and connective tissue disorders. Attempts at identifying a common molecular etiology for the characteristic features of STLS were unsuccessful until 2015 when Gonzaga-Jauregui et al. reported that the COL27A1 p.Gly697Arg variant, when in homozygosity, is a molecular cause of Steel Syndrome and suggested that this missense change is a founder variant in individuals of Puerto Rican descent (Gonzaga-Jauregui et al., Europ. J. Hum. Genet. 23: 342-346, 2015), Subsequent studies in large cohorts including multi-ethnic populations have identified the p.Gly697Arg variant in additional individuals. Additional cases have been published linking novel rare recessive mutations in COL27A1 with osteochondrodysplastic phenotypes manifesting features overlapping those of the reported Puerto Rican patients with Steel Syndrome, but also with additional features not attributed to Steel Syndrome, such as hearing loss and speech delay (Gariballa et al., Am J Med Genet A. 2017; 173(5):1257-1263; Kotabagi et al., Clin Genet. 2017; 92(3):323-326).

SUMMARY OF THE DISCLOSURE

This disclosure relates to a rodent model of Steel Syndrome. More specifically, this disclosure provides genetically modified rodent animals (e.g., mouse or rat) that carry a mutation in an endogenous rodent Col27a1 gene, equivalent to a mutation in the human COL27A1 gene causing Steel Syndrome in humans.

In some embodiments, disclosed herein is a genetically modified rodent, whose genome comprises a mutation in an endogenous rodent Col27a1 gene, wherein the mutation is equivalent to the mutation in a human COL27A1 gene resulting in a Gly to Arg substitution at amino acid position 697 (G697R) of the human COL27A1 protein.

In some embodiments, the rodent is a mouse or a rat. In certain embodiments, the rodent is a mouse and the mutation in the endogenous mouse Col27a1 gene results in a Gly to Arg substitution at amino acid position 682 in the mouse Col27a1 protein. In other embodiments, the rodent is a rat and the mutation in the endogenous rat Col27a1 gene results in a Gly to Arg substitution at amino acid position 691 in the rat Col27a1 protein.

In some embodiments, the rodent is heterozygous for a mutation in an endogenous rodent Col27a1 gene. In other embodiments, the rodent is homozygous for a mutation in an endogenous rodent Col27a1 gene.

Rodent animals disclosed herein, particularly rodents that are homozygous for a mutation equivalent to a mutation encoding the G697R variation in the human COL27A1 protein, or heterozygous for the mutation but incapable of expressing a wild type rodent Col27a1 protein, exhibit one or more abnormalities associated with Steel Syndrome. In some embodiments, the abnormalities are selected from the group consisting of severe thoracic kyphosis in the vertebral column at 3 weeks of age, decreased body length, decreased lengths of long bones, lowered bone mineral content (BMC), and reduced body weight, as compared to a wild type rodent animal.

In some embodiments, disclosed herein is an isolated cell or tissue of a rodent, whose genome comprises a mutation in an endogenous rodent Col27a1 gene, wherein the mutation is equivalent to the mutation in a human COL27A1 gene resulting in a G697R substitution in the human COL27A1 protein. The isolated cell or tissue can be that of a mouse or a rat.

In some embodiments, disclosed herein is an isolated rodent embryonic stem cell, whose genome comprises a mutation in an endogenous rodent Col27a1 gene, wherein the mutation is equivalent to the mutation in a human COL27A1 gene resulting in a G697R substitution in the human COL27A1 protein. The isolated rodent embryonic stem cell can be a mouse or rat embryonic stem cell.

In some embodiments, disclosed herein is a method of making a Col27a1 mutant rodent, comprising modifying a rodent genome so that the modified genome comprises a mutation in the endogenous rodent Col27a1 gene that is equivalent to the mutation in a human COL27A1 gene resulting in a G697R substitution in the human COL27A1 protein; and making a Col27a1 mutant rodent comprising the modified genome. In some embodiments, the rodent genome is modified by introducing a targeting nucleic acid into the genome of a rodent ES cell to obtain a mutant rodent ES cell whose genome comprises the mutation in the endogenous rodent Col27a1 gene; and making a Col27a1 mutant rodent using the mutant rodent ES cell of (a). The present method can be used to make a mutant mouse or a rat.

In some embodiments, disclosed herein is a targeting nucleic acid construct, comprising a nucleic acid sequence to be integrated into a rodent Col27a1 gene at an endogenous rodent Col27a1 locus, flanked by a 5' nucleotide sequence and a 3' nucleotide sequence that are homologous to nucleotide sequences at the rodent Col27a1 locus, wherein integration of the nucleic acid sequence into the rodent Col27a1 gene results in a mutation in the endogenous rodent Col27a1 gene that is equivalent to the mutation in a human COL27A1 gene resulting in a G697R substitution in the human COL27A1 protein. The targeting nucleic acid construct can be designed for integrating the nucleic acid sequence into a mouse or rat Col27a1 gene at an endogenous mouse or rat Col27a1 locus.

In further embodiments, disclosed herein is a method of identifying a therapeutic agent for the treatment of Steel Syndrome, the method comprising administering an agent to a rodent disclosed herein, performing one or more assays to determine if the agent has an effect on one or more abnormalities associated with Steel Syndrome in the rodent; and identifying the agent as a therapeutic agent when the agent has a therapeutic effect on the one or more abnormalities associated with Steel Syndrome. In some embodiments, the agent is administered to the rodent at or shortly after birth, for example, within 15, 14, 13, 12, 11, 10, 9, 8, 7, 6, 5, 4, 3, 2 days or 1 day after birth.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIGS. 5A-5D set forth alignment of human, mouse and rat Col27a1 protein sequences (SEQ ID NOS: 2, 4 and 6, respectively). Glycine 697 in human COL27A1, Glycine 682 in mouse Col$^{27}$a1, and Gly 691 in rat Col27a1 are highlighted (at position numbered as 708).

DETAILED DESCRIPTION

Figure 1:
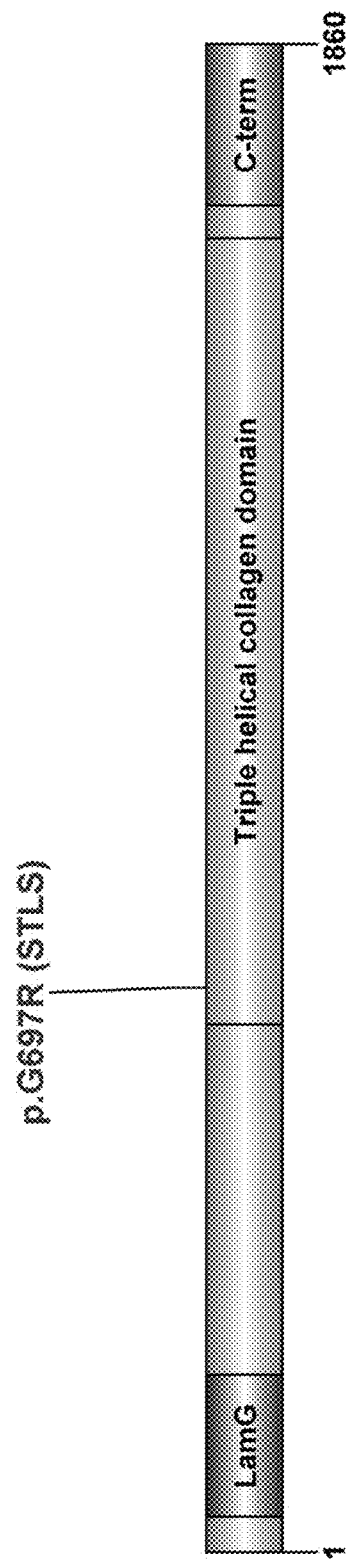
FIG. 1 depicts the domain structure of the human COL27A1 protein (the Laminin G domain, the triple helical domain characteristic of collagen proteins, and the fibrillar collagen C-term domain), as well as the location of the pG697R mutation.

Disclosed herein is a rodent animal model of Steel Syndrome. In particular, disclosed herein are rodent animals having a mutation in an endogenous rodent Col27a1 gene, equivalent to a mutation in the human COL27A1 gene, e.g., p.Gly697Arg, which causes Steel Syndrome in humans. The rodent animals disclosed herein recapitulate clinical features observed in humans having Steel Syndrome, and are useful for the identification and development of therapeutic candidates for the treatment and/or amelioration of Steel Syndrome and other bone disorders.

Various aspects of the present disclosure are described in detail in the following sections.

COL27A1

Collagens are the most abundant proteins in the extracellular matrix and the major contributors to the structure and scaffolding of connective tissues in vertebrates. Collagen proteins can be subdivided into different families, but all share a similar structure characterized by triple helical domains of the repeating triple amino acids (Gly-Xaa-Yaa) (Gariballa et al., Am J Med Genet A. 2017; 173(5):1257-1263; Gonzaga-Jauregui et al., supra).

Collagen type XXVII, alpha 1 COL27A1) is a member of the fibrillar collagen family. Collagen type XXVII is highly expressed in the developing cartilage and to a lesser extent in other tissues (Pace et al., Matrix Biol. 22: 3-14, 2003; Boot-Handford et al., J. Biol. Chem. 278: 31067-77, 2003; Plumb et al., J. Biol. Chem. 282: 12791-12795; 2007; and Hjorten et al., Bone 41: 535-542, 2007). Based on the expression pattern, it has been hypothesized that COL27A1 may play an important role during cartilage mineralization, providing a scaffold for the entry of other cell types and invasion of blood vessels in order to form bone structures. Zebra fish and mice have been utilized to study the effects of potential loss of function of the Col27a1 gene. These studies suggest that COL27A1 plays an important role in the skeletal system formation and development (Christiansen et al., PLoS ONE 4(12): 1-10, 2009; Plumb et al., PLoS ONE 9422, 2011).

The human COL27A1 gene is located at 9q32-33, about 156 kb in length, and composed of 61 exons, and encodes a pro-peptide of 1860 amino acids. The protein has the characteristic structure of collagens; however, its triple helical domain is shorter (990 amino acids) as compared to other proalpha collagen proteins (1012 amino acids). The homologous mouse gene is located on chromosome 4 and encodes a protein of 1845 amino acids. Col27a1 is highly conserved across species. For example, both the human and mouse COL27A1 proteins include a signal peptide, a Laminin (1 domain (175 residues for human and 178 residues for mouse), a triple helical domain (994 residues for human, and 997 residues for mouse, with two conserved interruptions in the Gly-X-Y repeat), and an NCI domain or C-propeptide (239 residues for human and 242 residues for mouse, with 8 characteristic cysteine residues). See Table 1 (Summary description of features in Col27A1 proteins from human, mouse and rat) and FIGS. 5A-5D (alignment of human, mouse and rat Col27A1 protein sequences).

Exemplary COL27A1 mRNA and protein sequences from human, mouse and rat are available in GenBank under the following accession numbers, and are also set forth as SEQ ID NOS: 1-6 in the Sequence Listing.

TABLE 1

| SEQ ID NO | Description | Features |
|---|---|---|
| 1 | *Homo sapiens* COL27:A1 mRNA, NM_032888.3 | Length: 7818 bp<br>CDS: 407-5989<br>polyA signal sequence: 7777-7782<br>polyA site: 7810 |
| 2 | *Homo sapiens* COL27A1 protein, NP_116277.2 | Length: 1860 aa<br>Signal peptide: 1-41 |

TABLE 1-continued

| SEQ ID NO | Description | Features |
|---|---|---|
| | | Proprotein: 42-1860<br>Mature protein: 625-1621<br>LamG domain: 45-220<br>Triple helical region: 625-1618<br>Fibrillar collagen<br>C-terminal domain: 1661-1859 |
| 3 | *Mus musculus* Col27a1 mRNA, NM_025685.3 | Length: 7635 bp<br>CDS: 415-5952 |
| 4 | *Mus musculus* Col27a1 protein, NP_079961.3 | Length: 1845 aa<br>Signal peptide: 1-39<br>Mature protein: 610-1606<br>LamG domain: 43-221<br>Triple helical region: 610-1603<br>Fibrillar collagen<br>C-terminal domain 646-1844 |
| 5 | *Rattus norvegicus* Col27a1 mRNA, NM_198747.1 | Length: 5568 bp<br>CDS: 1-5568 |
| 6 | *Rattus norvegicus* Col27a1 protein, NP_942042.1 | Length: 1855 aa<br>Signal peptide: 1-48<br>Mature protein: 619-1612<br>LamG domain: 52-230<br>Triple helical region: 619-1612<br>Fibrillar collagen<br>C-terminal domain: 1656-1854 |

Steel Syndrome and Pathogenic Mutation in Human COL27A1

Steel Syndrome (MIM #615155) was first described by Steel et al. in 1993 as an orthopedic syndrome observed in 23 Hispanic children from Puerto Rico (Steel et al., J. Bone Joint Surg. Am. 75: 259-264, 1993). The main clinical features include congenital bilateral hip and radial head dislocation, short stature, carpal coalitions, scoliosis, foot abnormalities, and mildly dysmorphic features. Standard treatment for congenital hip dislocation is surgical intervention, which generally has poor outcome (Gonzaga-Jauregui et al., Europ. J. Hum. Genet. 23: 342-346, 2015).

The term "mutation" includes an addition, deletion, or substitution of one or more nucleotides in a gene. In some embodiments, a mutation is a substitution of a single nucleotide. In other embodiments, a mutation is a deletion of one or more nucleotides. In some embodiments, a mutation in a gene results in an addition, deletion, or substitution of one or more amino acids in the encoded protein to provide a mutant protein. In some embodiments, a mutation in a gene causes a substitution of an amino acid in the encoded protein. In other embodiments, a mutation in a gene causes a deletion of one or more amino acids. In certain embodiments, a mutation in a gene (e.g., a substitution of a nucleotide) is a nonsense mutation, i.e., the change codes for an early termination codon resulting in a truncated protein. In some embodiments, a mutation in a gene, e.g., an addition or deletion of one or more nucleotides, causes a frameshift in the reading frame, resulting in a mutant protein that is truncated or elongated, or has a different amino acid sequence, as compared to the wild type protein product. In still other embodiments, a mutation in a gene can also affect splicing, e.g., by changing the donor or acceptor site, resulting in a differently spliced mRNA transcript and consequently a different protein product.

In accordance with this disclosure, a mutation in the human COL27A1 gene causing Steel Syndrome is a mutation in the human COL27A1 gene that is linked and segregates with Steel Syndrome. Such mutation is also referred to herein as a pathogenic mutation.

Mutation in human COL27A1 was first linked to Steel Syndrome in 2015 when Gonzaga-Jauregui et al. identified a homozygous rare missense variant (c.2089G>C, in exon 7; p.G697R) in the COL27A1 gene shared by two siblings and their affected cousin, all having Steel Syndrome (Gonzaga-Jauregui et al., Europ. J. Hum. Genet. 23: 342-346, 2015). This variant had been reported earlier at low frequencies in the heterozygous state in population databases and did not appear to have any visible phenotypic effect in the heterozygous carriers. Gonzaga-Jauregui et al. concluded that when in homozygosity, the COL27A1 p.Gly697Arg variant is a molecular cause of Steel Syndrome.

Subsequent studies in large cohorts including multi-ethnic populations have identified the p.Gly697Arg variant in additional individuals (Belbin et al., eLife 2017; 6. pii:e25060). The study described in the Examples herein demonstrate homozygosity and segregation of this variant with multiple affected individuals, further confirming that the variant allele represents a founder mutation and is the molecular cause of Steel Syndrome.

The p.Gly697Arg variant is a substitution that changes a highly conserved Glycine residue that is part of the Gly-Xaa-Yaa repeat motif characteristic of the triple helical domain of collagen proteins. See, e.g., FIG. 3(b)-(c) of Gonzaga-Jauregui et al., supra. Without being bound to any particular theory, the Gly697Arg substitution may result in misfolding of the protein resulting in abnormal function when secreted into the extracellular matrix of the hypertrophic region of the bone growth plate resulting in the abnormal growth phenotype observed in human patients and the rodent mouse model.

Rodents Comprising a Mutation in Endogenous Col27a1 Equivalent to a Mutation Causing Steel Syndrome in Humans As demonstrated herein, a mutation equivalent to a mutation in the human COL27A41 gene causing Steel Syndrome can be introduced into an endogenous Col27a1 gene in a rodent and causes the rodent to exhibit features observed in humans, such as the skeletal abnormalities characteristic of Steel Syndrome.

In some embodiments, a pathogenic mutation in the human COL27A1 gene is a missense mutation. In some embodiments, the pathogenic mutation in the human COL27A1 gene is a mutation that results in a substitution of Glycine with Arginine at amino acid position 697 of human COL27A1.

By "equivalent", it is meant that a mutation in a rodent Col27a1 gene results in the same missense substitution as in humans, e.g., a substitution Glycine with Arginine, at an amino acid position in the rodent Col27a1 protein corresponding to amino acid position 697 in the human COL27A1 protein. For example, a mutation in a mouse Col27a1 gene that is equivalent to the Gly697Arg human mutation is a mutation resulting in a Gly to Arg substitution at position 682 of the mouse Col27a1 protein, according to Accession No. NP_079961.3 and a mutation in a rat Col27a1 gene that is equivalent to the Gly697Arg human mutation is a mutation resulting in a Gly to Arg substitution at position 691 of the rat Col27a1 protein, according to Accession No. NP_116277.2

One can easily determine amino acid positions in a rodent Col27a1 protein that correspond to given amino acid positions in a human COL27A1 protein. Various sequence alignment tools are available in the art, including those available in commercial computer programs such as BLASTN for nucleotide sequences, and BLASTP, gapped BLAST, and PSI-BLAST for amino acid sequences. Exemplary programs are described in Altschul, S. F. et al., 1997, Methods in Enzymology; Baxevanis, A. D., and B. F. F.

Ouellette (eds.) Bioinformatics: A Practical Guide to the Analysis of Genes and Proteins, Wiley, 1998; and Misener et al. (eds.) Bioinformatics Methods and Protocols (Methods in Molecular Biology, Vol. 132), Humana Press, 1998. To illustrate, an alignment of a human COL27A1 protein (SEQ ID NO: 2), a mouse Col27a1 protein (SEQ ID NO: 4), and rat Col27a1 (SEQ ID NO: 6) using the multiple global sequence alignment ClustalW program is provided in FIG. 5A-5D.

In some embodiments, a rodent animal disclosed herein that contains a mutation in an endogenous rodent Col27a1 gene equivalent to a pathogenic mutation in the human COL27A1 gene can be heterozygous or homozygous for this mutation.

In some embodiments, a rodent animal disclosed herein is incapable of expressing a wild type rodent Col27a1 protein. For example, a rodent is provided where one copy of the endogenous rodent Col27a1 gene contains a mutation equivalent to a pathogenic human mutation and the other copy is disrupted or deleted. Alternatively, the rodent animal is homozygous for a mutation equivalent to a pathogenic mutation in the human COL27A1 gene, and is consequently incapable of expressing a wild type rodent Col27a1 protein.

Rodent animals provided herein, as a result of carrying a mutation equivalent to a pathogenic mutation in human COL27A1 and incapable of expressing a wild type Col27a1 protein, exhibit features observed in humans characteristic of Steel Syndrome. In some embodiments, rodent animals disclosed herein exhibit one or more abnormalities characteristic of Steel Syndrome in humans such as, for example, one or more of the following skeletal abnormalities: severe thoracic kyphosis in the vertebral column demonstrated at 3 weeks of age, decreased body length, decreased lengths of the long bones, lowered bone mineral content (BMC), defects in growth plates, and reduced body weight, as compared to wild type (control) rodents. In some embodiments, craniofacial abnormalities in the subject rodent animals include shorter snout and slightly rounded dome shaped skull, which can be observed as early as in the embryonic stage (e.g., embryonic day 18.5). In some embodiments, defects in the growth plates in a rodent include loss of the normal architecture of proliferative zone with absence and/or disorganization of columnar chondrocytes. The differences between a mutant rodent and a wild type rodent in any of the above-mentioned parameters are significant, i.e., a parameter in a mutant rodent animal differs from the same parameter in wild type rodents by at least about 15%, 200%, 25%, 30%, 40%, 45%, 50%, 55%, 60%, 65%, 70%, 75%, or more.

The rodents provided herein include, for example, mice, rats, and hamsters. In some embodiments, the rodent is a mouse or a rat. In specific embodiments, the rodent is a mouse.

In some embodiments, the rodent is a mouse of a C57BL strain, for example, a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In other embodiments, the rodent is a mouse of a 129 strain, for example, a 129 strain selected from the group consisting of 129P1, 129P2, 129P3, 129X1, 129S1 (e.g., 129S1/SV, 129S1/SvIm), 129S2, 129S4, 129S5, 129S9/SvEvH, 129/SvJae, 129S6 (129/SvEvTac), 129S7, 129S8, 129T1, 129T2 (see, e.g., Festing et al. (1999), Mammalian Genome 10:836; Auerbach et al. (2000), Biotechniques 29(5):1024-1028, 1030, 1032). In some embodiments, the rodent is a mouse that is a mix of an aforementioned 129 strain and an aforementioned C57BL/6 strain. In certain embodiments, the mouse is a mix (i.e., hybrid) of aforementioned 129 strains, or a mix of aforementioned C57BL strains, or a mix of a C57BL strain and a 129 strain. In certain embodiments, the mouse is a mix of a C57BL/6 strain with a 129 strain. In specific embodiments, the mouse is a VGF1 strain, also known as F1H4, which is a hybrid of C57BL/6 and 129. In other embodiments, the mouse is a BALB strain, e.g., BALB/c strain. In some embodiments, the mouse is a mix of a BALB strain and another aforementioned strain.

In some embodiments, the rodent is a rat. In certain embodiments, the rat is selected from a Wistar rat, an LEA strain, a Sprague Dawley strain, a Fischer strain, F344, F6, and Dark Agouti. In other embodiments, the rat is a mix of two or more strains selected from the group consisting of Wistar. LEA, Sprague Dawley, Fischer, F344, F6, and Dark Agouti.

Targeting Vectors and Methods for Making a Rodent Comprising a Mutation

The rodents provided herein can be made using the methods disclosed herein. In exemplary embodiments, a targeting vector carrying a rodent Col27a1 nucleic acid sequence containing a desired mutation is constructed. The targeting vector can include, in addition to a mutation-containing rodent Col27a1 nucleic acid sequence, flanking nucleic acid sequences that are of suitable lengths and homologous to rodent Col27A1 gene sequences at an endogenous rodent Col27a1 locus so as to be capable of mediating homologous recombination and integration of the mutation-containing rodent Col27A1 nucleic acid sequence into the endogenous rodent Col27a1 gene.

In some embodiments, a nucleic acid molecule (e.g., an insert nucleic acid) comprising a rodent Col27a1 gene mutation is inserted into a vector, preferably a DNA vector. Depending on size, a mutant rodent Col27a1 gene sequence can be cloned directly from cDNA sources or designed in silico based on published sequences available from GenBank (see above). Alternatively, bacterial artificial chromosome (BAC) libraries can provide rodent Col27a1 gene sequences. Rodent Col27A1 gene sequences may also be isolated, cloned and/or transferred from yeast artificial chromosomes (YACs).

In some embodiments, the insert nucleic acid also contains a selectable marker gene (e.g., a self deleting cassette containing a selectable marker gene, as described in U.S. Pat. Nos. 8,697,851, 8,518,392 and 8,354,389, all of which are incorporated herein by reference), which can be flanked by or comprises site-specific recombination sites (e.g., loxP, Frt, etc.). The selectable marker gene can be placed on the vector adjacent to the mutation to permit easy selection of transfectants.

Figure 4:
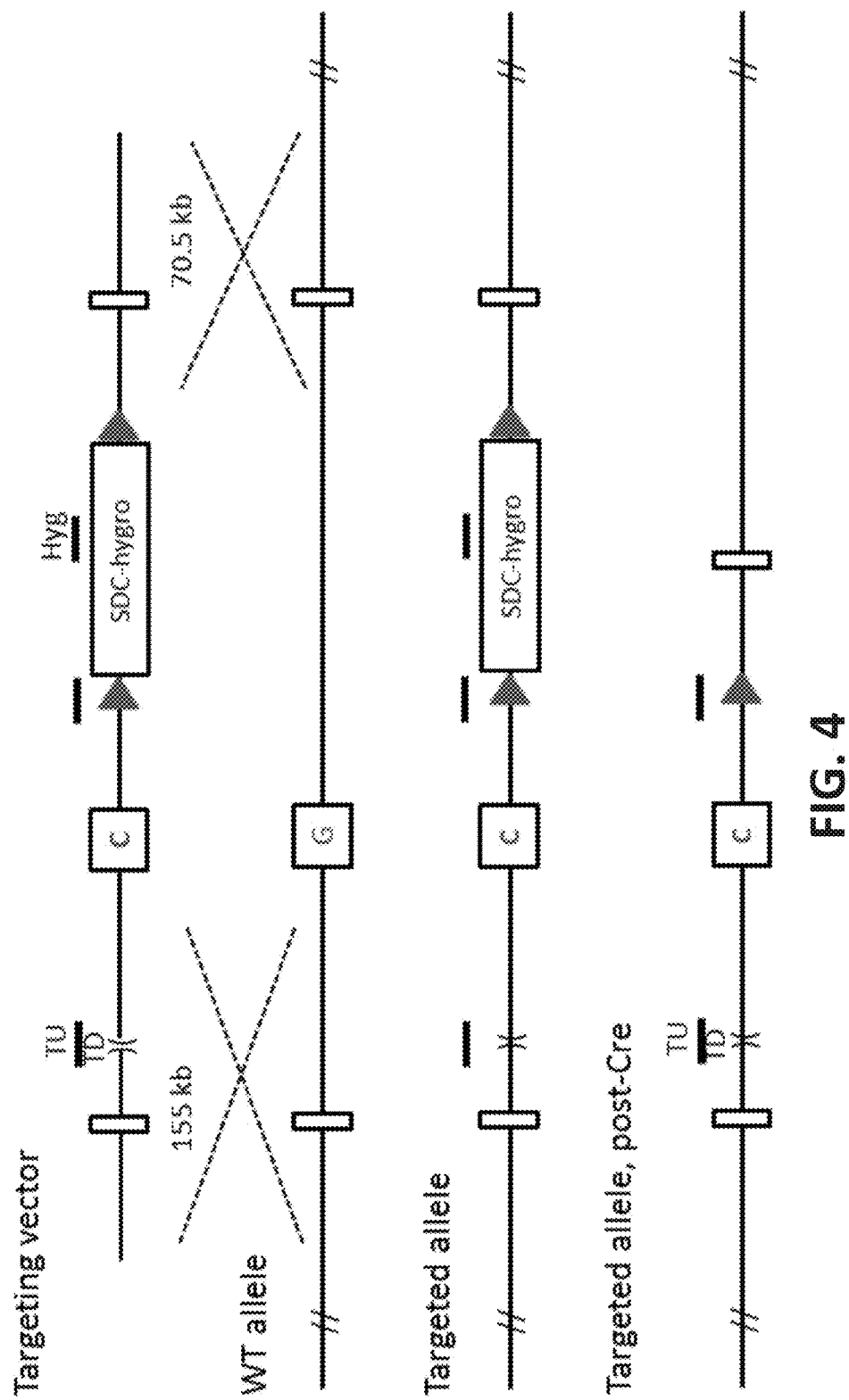
FIG. 4 depicts an exemplary targeting strategy for introducing the G697R orthologous mutation (G682R) into a wild type Col27a1 allele in a mouse.

An exemplary targeting vector is shown in FIG. 4.

In some embodiments, a BAC vector carrying a mutant rodent Col27a1 gene sequence can be introduced into rodent embryonic stem (ES) cells by, e.g., electroporation. Both mouse ES cells and rat ES cells have been described in the art. See, e.g., U.S. Pat. Nos. 7,576,259, 7,659,442, 7,294,754, and US 2008-0078000 A1 (all of which are incorporated herein by reference) describe mouse ES cells and the VELOCIMOUSE® method for making a genetically modified mouse; and US 2014/0235933 A1 and US 2014/0310828 A1 (all of which are incorporated herein by reference) describe rat ES cells and methods for making a genetically modified rat.

Homologous recombination in recipient cells can be facilitated by introducing a break in the chromosomal DNA at the integration site, which may be accomplished by targeting certain nucleases to the specific site of integration. DNA-binding proteins that recognize DNA sequences at the target locus are known in the art. In some embodiments, zinc finger nucleases (ZFNs), which recognize a particular 3-nucleotide sequence in a target sequence, are utilized. In some embodiments, Transcription activator-like (TAL) effector nucleases (TALENs) are employed for site-specific genome editing. In other embodiments, RNA-guided endonucleases (RGENs), which consist of components (Cas9 and tracrRNA) and a target-specific CRISPR RNA (crRNA), are utilized.

In some embodiments, a targeting vector carrying a nucleic acid of interest (e.g., a nucleic acid containing a mutation to be introduced), flanked by 5' and 3' homology arms, is introduced into a cell with one or more additional vectors or mRNA. In one embodiment, the one or more additional vectors or mRNA contain a nucleotide sequence encoding a site-specific nuclease, including but not limited to a zinc finger nuclease (ZFN), a ZFN dimer, a transcription activator-like effector nuclease (TALEN), a TAL effector domain fusion protein, and an RNA-guided DNA endonuclease.

ES cells having the mutant gene sequence integrated in the genome can be selected. After selection, positive ES clones can be modified, e.g., to remove a self-deleting cassette, if desired. ES cells having the mutation integrated in the genome are then used as donor ES cells for injection into a pre-morula stage embryo (e.g., 8-cell stage embryo) by using the VELOCIMOUSE® method (see, e.g., U.S. Pat. Nos. 7,576,259, 7,659,442, 7,294,754, and US 2008/0078000 A1), or methods described in US 2014/0235933 A1 and US 2014/0310828 A1. The embryo comprising the donor ES cells is incubated until blastocyst stage and then implanted into a surrogate mother to produce an F0 rodent fully derived from the donor ES cells. Rodent pups bearing the mutant allele can be identified by genotyping of DNA isolated from tail snips using a modification of allele (MOA) assay (Valenzuela et al., supra) that detects the presence of the mutant sequence or a selectable marker gene.

Use as a Rodent Model of Steel Syndrome

The rodents provided herein permit a better understanding of the molecular mechanisms underlying the development of Steel Syndrome. In addition, such rodents may be used in the screening and development of therapeutic agents for the prevention and treatment of Steel Syndrome and other bone disorders (e.g., growth deficiency, arthritis, osteoporosis, scoliosis, cervicalgia, among others).

In some embodiments, an effect of a candidate therapeutic agent is determined in vivo, by administering the agent to a rodent disclosed herein, i.e., a rodent carrying a mutation in the endogenous rodent Col27a1 gene that is equivalent to a pathogenic mutation in the human COLA27A1 gene. In some embodiments, a candidate therapeutic agent is a nucleic acid molecule, e.g., a COL27A1 gene therapy drug.

In some embodiments, rodent animals described herein are used to determine and/or optimize vector design of one or more candidate gene therapy drugs.

In some embodiments, rodent animals described herein are used to determine the pharmacokinetic properties of a candidate drug, e.g., a gene therapy drug. Pharmacokinetic properties include, but are not limited to, how a non-human animal processes the drug into various metabolites (or detection of the presence or absence of one or more drug metabolites, including, but not limited to, toxic metabolites), drug half-life, circulating levels of drug after administration (e.g., serum concentration of drug), anti-drug response (e.g., anti-drug antibodies), drug absorption and distribution, route of administration, routes of excretion and/or clearance of the drug.

Candidate drugs, e.g., COL27A1 gene therapy drugs, may be dosed via any desired route of administration including parenteral and non-parenteral routes of administration for evaluation in non-human animals described herein. Parenteral routes include, e.g., intravenous, intraarterial, intraportal, intramuscular, subcutaneous, intraperitoneal, intraspinal, intrathecal, intracerebroventricular, intracranial, intrapleural or other routes of injection. Non-parenteral routes include, e.g., oral, nasal, transdermal, pulmonary, rectal, buccal, vaginal, ocular. Administration may also be by continuous infusion, local administration, sustained release from implants (gels, membranes or the like), and/or intravenous injection. Various assays may be performed to determine the pharmacokinetic profiles of administered drugs using samples obtained from rodent animals described.

In some embodiments, candidate drugs, e.g., gene therapy drugs, are given to a rodent animal described herein at birth or shortly after birth, e.g., within 15, 14, 13, 12, 11, 10, 9, 8, 7, 6, 5, 4, 3, 2 days or 1 day after birth. Various functional and/or morphological assays or analyses can be performed at various time points (e.g., 0 hour, 6 hours, 1 day, 2 days, 3 days, 4 days, 5 days, 10 days, 15 days, 30 days, 60 days, 90 days, to up to 6-12 months or more), to determine the effect of a candidate drug in inhibiting the development and/or progression of the abnormalities described herein for rodents carrying a Col27a1 mutation equivalent to a pathogenic mutation in humans.

In some embodiments, performing an assay includes determining the differences between a mutation-carrying rodent animal administered a drug and either (i) a mutation-carrying rodent animal not administered the drug, (ii) a rodent heterozygous for the mutation, and/or a rodent without the mutation (i.e., a wild-type rodent animal).

The present description is further illustrated by the following examples, which should not be construed as limiting in any way. The contents of all cited references (including literature references, issued patents, and published patent applications as cited throughout this application) are hereby expressly incorporated by reference.

Example 1. Confirmation of the COL27A1 (p.Gly697Arg) Variant in Additional Steel Syndrome Patients A rare COL27A1 missense variant, p.Gly697Arg, was initially found to be present in homozygosis in three members of a single family having Steel Syndrome and was subsequently confirmed to be the molecular cause of the disease.

Samples from 6 of the original STLS patients reported by Steel in 1993 and their available family members were obtained and genotyped. Five of the six patients were found to be homozygous for this same p.Gly697Arg variant and that it segregates in these Puerto Rican families according to Mendelian expectations for an autosomal recessive disorder. Further, samples from 4 additional patients of Puerto Rican descent with suspected Steel Syndrome based on clinical presentation were also analyzed by whole-exome sequencing and targeted mutation testing. These individuals were also found to be homozygous for the p.Gly697Arg variant in COL27A1.

Altogether, a total of 40 patients have been reported in the literature with clinical findings corresponding to "The Puerto Rican syndrome" that Steel reported 50 years ago. Of these 17 have been molecularly confirmed and reported to be homozygous for the p.Gly697Arg variant in COL27A1, all of Puerto Rican ancestry, confirming the founder effect hypothesis for this disorder. The reported cases also document the specificity of the genotype-phenotype association consistent with a relatively uniform clinical phenotype characterized primarily by short stature, bilateral congenital hip dysplasia, carpal coalitions, radial head dislocations, scoliosis, foot deformities and vertebral anomalies.

Example 2. In Vivo Mouse Modeling of the Steel Syndrome p.Gly697Arg Variant

Generation of Col27a1 Mutant Mice.

To model the human p.Gly697Arg variant, a guanine-to-cytidine mutation, resulting in a p.Gly682Arg substitution (orthologous to the human mutation), was introduced in the highly conserved triple helical domain of the murine Col27a1 gene. The mutation was introduced in exon 7 of the mouse gene using standard protocols for CRISPR/Cas9 gene editing and the VelociGene© method (Valenzuela et al., Nat Biotechnol. 2003; 21(6):652-9; Poueymirou et al., Nat Biotechnol. 2007; 25(1):91-9). FIG. 4 illustrates the targeting strategy. The final targeting vector was electroporated into C57BL/6N mouse embryonic stem cells, and selected via hygromycin resistance in the self-deleting cassette inserted in the downstream intron. Mice carrying the introduced mutation were confirmed by Sanger sequencing genotyping. Targeted, cassette-deleted knock-in mice were bred to obtain desired genotypes. Homozygous and heterozygous knock-in mice cohorts derived from F1 breeding were generated for phenotypic evaluation.

Growth and Skeletal Phenotyping.

Mice were monitored for growth kinetics by recording weight at specified time points and gross skeletal phenotyping was performed by biweekly imaging with in vivo μCT performed as previously described (Das N M, Hatsell S, Nannuru K, Huang L, Wen X, Wang L, Wang L H, Idone V, Meganck J A, Murphy A, Economides A, Xie L. In Vivo Quantitative Microcomputed Tomographic Analysis of Vasculature and Organs in a Normal and Diseased Mouse Model. PLoS One. 2016; 11(2):e0150085.) Briefly, whole body μCT imaging was performed using a high speed in vivo μCT scanner (Quantum F X, PerkinElmer, Hopkinton, Mass., USA). The X-ray source was set to a current of 88 μA, voltage of 90 kV. The CT imaging was visualized via 3D Viewer, existing software within the Quantum FX system. The field of view (FOV) was 60, and voxel size was 240 μm. Mice were kept under anesthesia during scanning. Specifically, anesthesia was induced by keeping the mice under 2.5-3% Isoflurane with 1.5 liter/min Oxygen flow for 2-3 minutes and then positioned on the scan platform. Constant delivery of isoflurane was achieved via a nose cone connected to the scan platform. Following the scanning process, mice were revived under a heating lamp and returned to their cages.

Bone mineral density (BMD) and bone mineral content (BMC) were calculated from the μCT scanned image data using Analyze software package (AnalyzeDirect, Overland Park, Kans., USA). Following scanning, image processing steps were undertaken. Image segmentation was performed semi-automatically using the Volume Edit tools within the Analyze software package (AnalyzeDirect, Overland Park, Kans., USA). Briefly, segmentation masks (object maps) were created using a combination of semi-automatic and manual techniques (object extraction, region growing and thresholding tools). These segmentation results were then manually modified if necessary and quantified using the ROI tools.

Results

Homozygous (Col27a1$^{G682R/G572R}$) KI mice displayed severe lethality before P7, with only a few pups surviving post weaning age. Phenotyping of homozygous KI embryos at E18.5 showed abnormal skull shape with a shortened snout but no significant differences in embryo size or length at this stage. Additionally, homozygous KI mice had abnormal lungs with poorly developed airspaces and thickened mesenchyme. Four homozygous KI mice survived past weaning age and were subjected to further evaluation for gross phenotypic and skeletal changes.

Figures 2A, 2B, 2C:
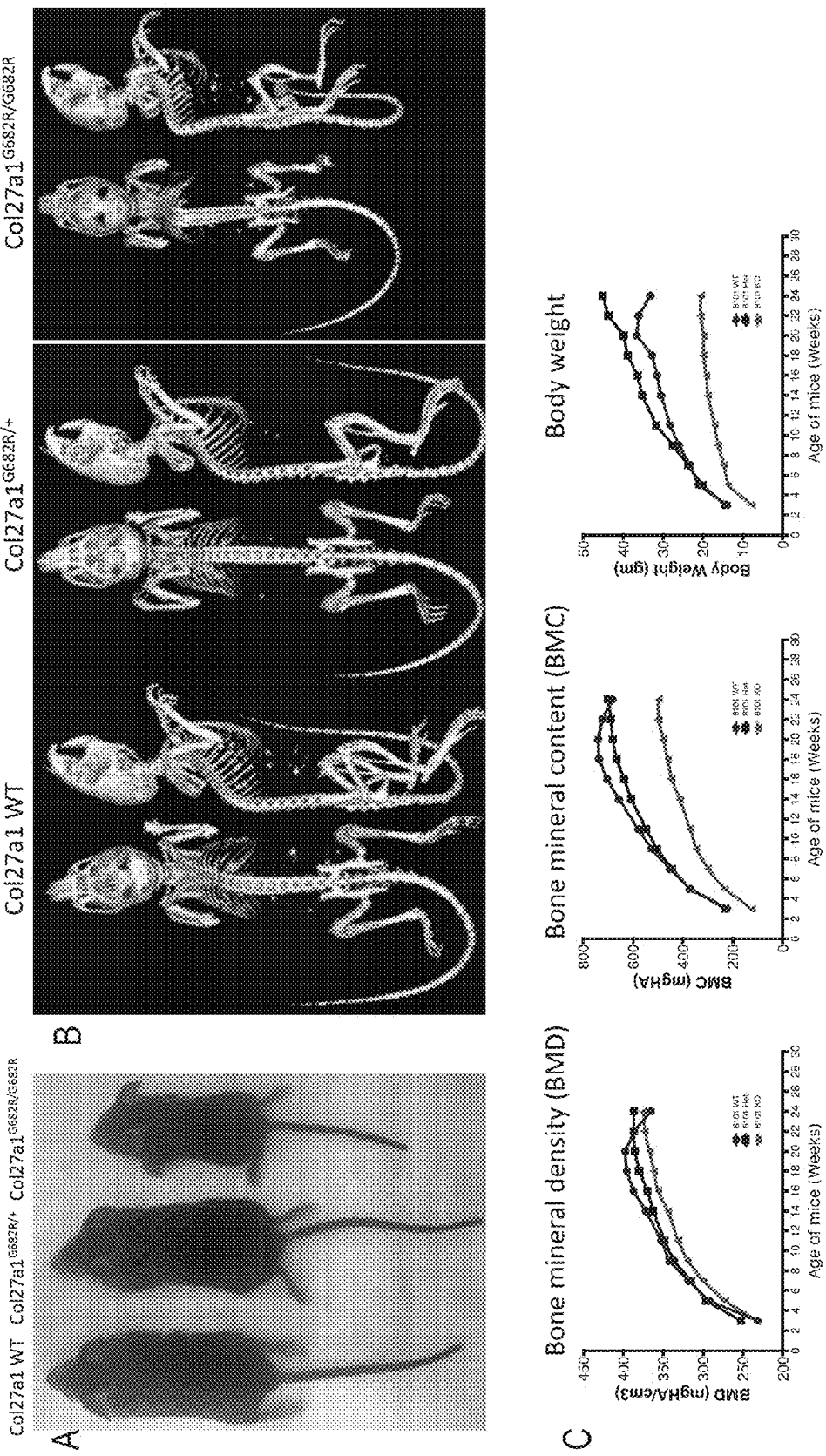
FIGS. 2A-2O depict the gross phenotype of Col27a1 knock-in mutant mice. (A) Homozygous Col27a1$^{G682R/G682R}$ mice displayed significant dwarfism, heterozygous Col27a1$^{G682R/+}$ mice were phenotypically normal and indistinguishable from wild-type littermates at 3 weeks of age. (B) Dorsal and lateral μCt images of mutant and wild type, where homozygous mutant mice displaying kyphosis, shorter snout and rounded skull. (C-D) Longitudinal monitoring of length, body weight, and skeletal parameters: bone mineral content (BMC) and bone mineral density (BMD) in homozygous and heterozygous KI mice versus wild-type littermates. Homozygous Col27a1$^{G682R/G682R}$ mice display decreased body weight and BIM.
Figure 2D:
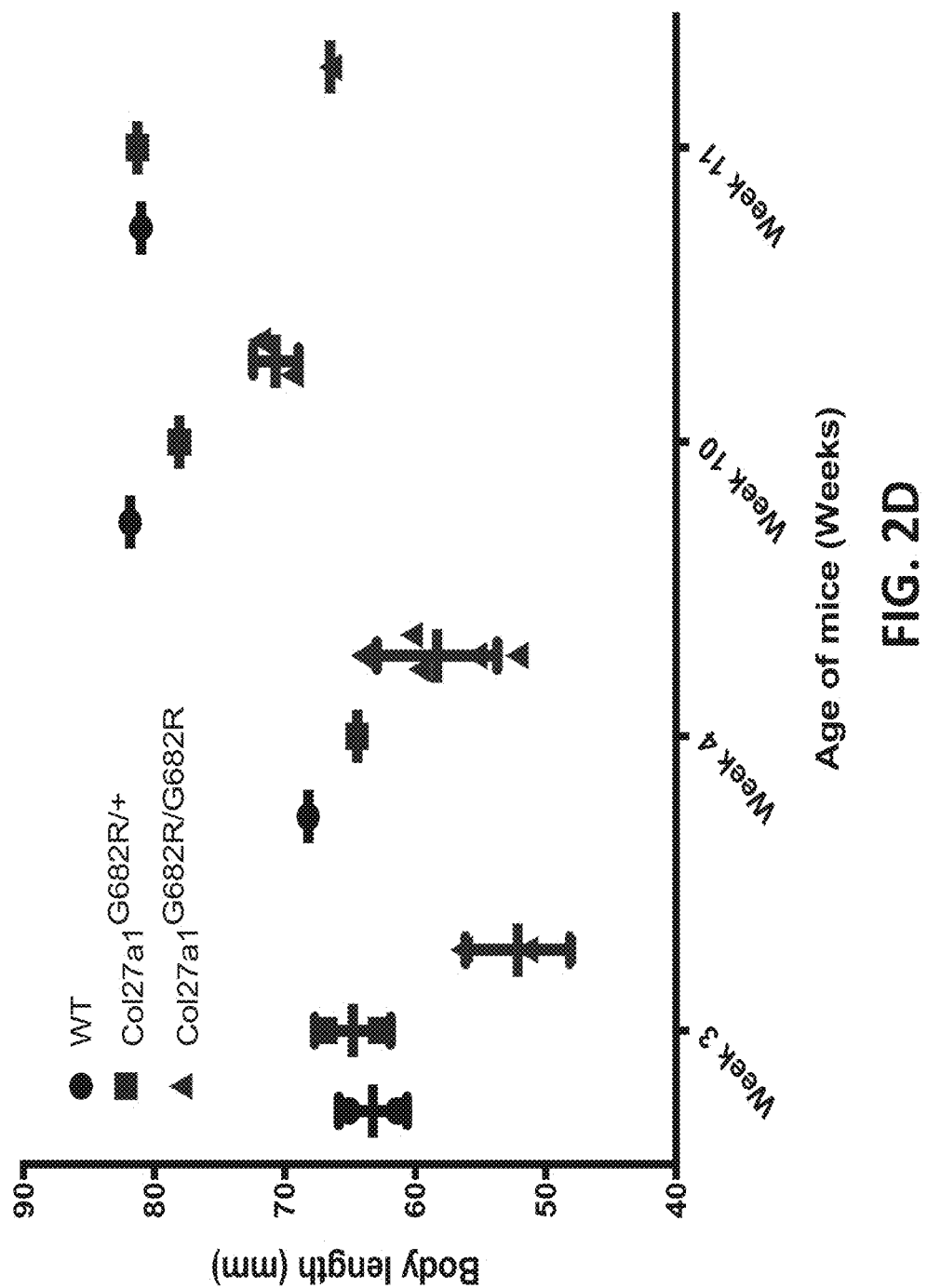

Computerized tomography (μCT) whole-body scans of heterozygous (Col27a1$^{G682R/+}$) and homozygous (Col27a1$^{G682R/G682R}$) KI mice and wild-type littermates were performed to evaluate for gross skeletal abnormalities and reduced length as a surrogate for the short stature phenotype observed in the human patients. The snout to base of the tail (at caudal vertebra 4, CA4) distance was measured to evaluate differences in length among the heterozygous, homozygous and wild-type mice. Homozygous mutant mice displayed evident severe dwarfism and were significantly smaller compared to wild-type or heterozygous littermates (FIG. 2A). Total body length was significantly decreased (FIG. 2B, 2D) and all the long bones were shorter. Homozygous KI mice also present with distinct craniofacial abnormalities including shorter snout and slightly rounded dome shaped skull, also observed early on in the embryonic stage. Analysis of the vertebral column demonstrated severe thoracic kyphosis at 3 weeks of age in all the homozygous KI mice evaluated, which lead to an acute angle between the skull and cervical vertebrae resulting in inward curvature of the rib cage. Analysis of skeletal parameters revealed that homozygous mutant mice displayed lower bone mineral content (BMC) as compared to heterozygous KI and wild-type mice (FIG. 2C). Homozygous mice were half the body weight compared wild-type litter mates, and their growth curve remained significantly lower throughout the monitoring period of 6 months compared wild-type and heterozygous litter mates. Heterozygous mice were viable and did not display any gross skeletal abnormalities; skeletal parameters were indistinguishable from wild-type littermates. Homozygous and heterozygous KI mice were monitored over a 6 month period; aging did not result in development of gross or detectable skeletal abnormalities at a later age in heterozygous mice.

Figure 3:
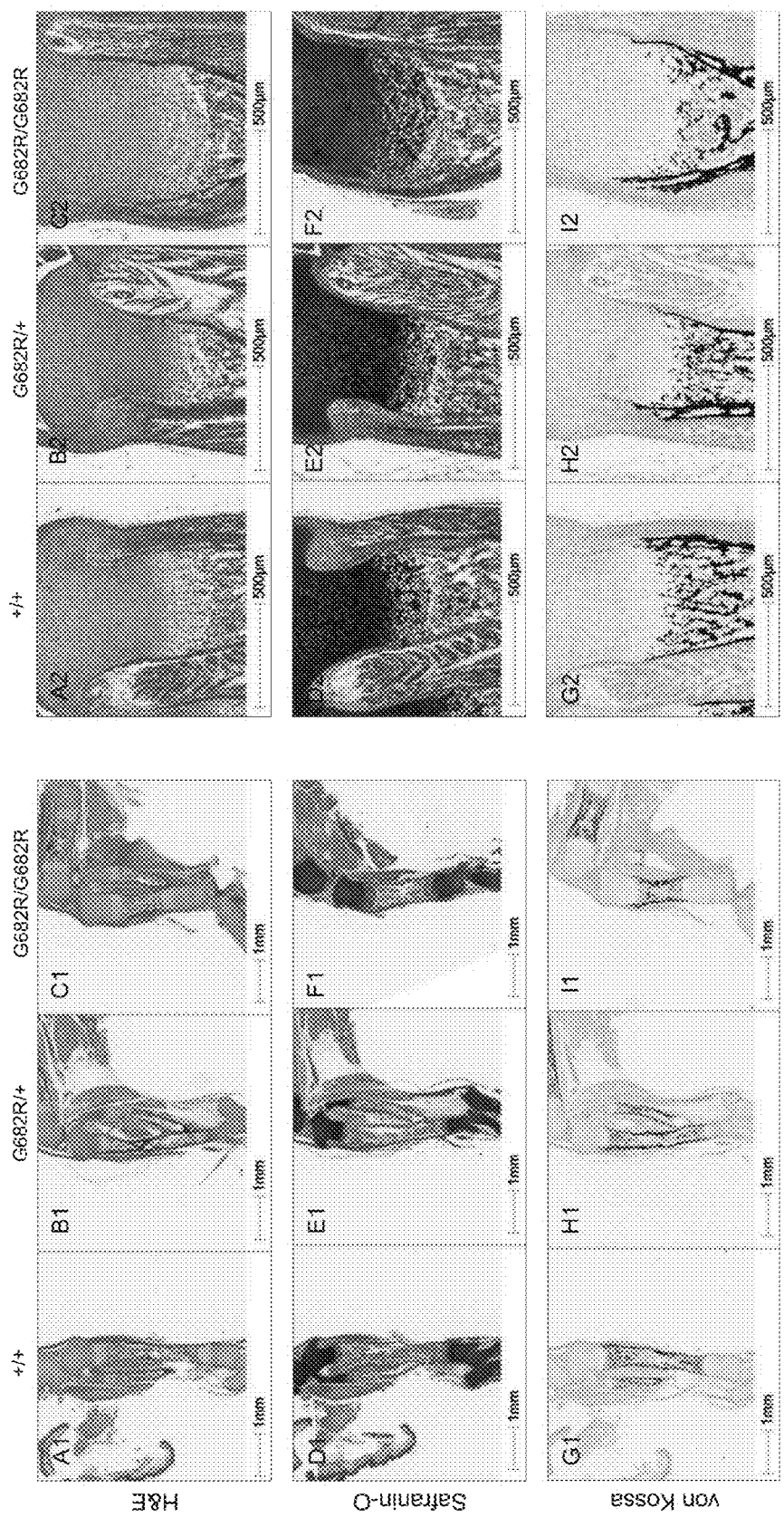
FIG. 3 shows histological analyses of long bones from Col27a1 G682R KI mice. Homozygous Col27a1$^{G682R/G682R}$ KI mice displayed chondrodysplasia with reduced and disorganized proliferative zone and complete absence of columnar chondrocytes as compared to wild-type and heterozygous KI littermates. Histochemical comparison of Safranin-O and von-Kossa stains displayed no overt differences in proteoglycan accumulation and mineralization respectively between genotypes.

Histological analyses of heterozygous (Col27a1$^{G682R/+}$) and homozygous (Col27a1$^{G682R/G682R}$) KI mice and wild-type littermates were performed to evaluate growth plate defects. Long bones (femurs and tibias) from heterozygous (Col27a1$^{G682R/+}$) and homozygous (Col27a1$^{G682R/G682R}$) KI mice, and wild-type littermates at P1 were collected, fixated and sectioned. Sections were then subjected to hematoxylin and eosin (H&E), Safranin-O or von Kossa staining according to standard protocols. Stained sections of femoral and tibial growth plates of homozygous KI mice showed complete loss of the normal architecture of proliferative zone with absence and disorganization of columnar chondrocytes (FIG. 3). Histochemical comparison of Safranin-O and von-Kossa stains displayed no overt differences in proteoglycan accumulation and mineralization in homozygous KI mice versus heterozygous KI and wild-type mice (FIG. 3). Interestingly, while the length and gross morphology of the long bones in heterozygous KI mice is no different from wild-type littermates, histological analyses of the growth plates in these mice revealed an intermediate phenotype, where the length of the proliferative zone of the growth plate was maintained but some disorganization in the columnar arrangement of chondrocytes can be observed (FIG. 3).

What is claimed is:

1. A genetically modified mouse, whose genome comprises a mutation in an endogenous mouse Col27a1 gene, wherein the mutation consists of a change of the codon encoding Gly at amino acid position 682 in the mouse Col27a protein to a codon encoding Arg, and wherein the mouse is heterozygous for the mutation.

2. A genetically modified mouse, whose genome comprises a mutation in an endogenous mouse Col27a1 gene, wherein the mutation consists of a change of the codon for Gly at amino acid position 682 in the mouse Col27a protein to a codon for Arg, wherein the mouse is homozygous for the mutation, wherein the mouse exhibits abnormalities associated with Steel Syndrome, and wherein the abnormalities associated with Steel Syndrome comprise decreased body length as compared to a wild type mouse.

3. An isolated mouse cell or tissue, whose genome comprises a mutation in an endogenous mouse Col27a1 gene, wherein the mutation consists of a change of the codon encoding Gly at amino acid position 682 in the mouse Col27a protein to a codon encoding Arg.

4. An isolated mouse embryonic stem (ES) cell, whose genome comprises a mutation in an endogenous mouse Col27a1 gene, wherein the mutation consists of a change of the codon encoding Gly at amino acid position 682 in the mouse Col27a protein to a codon encoding Arg.

5. A method of making a Col27a1 mutant mouse, comprising
   (a) introducing a targeting nucleic acid into the genome of a mouse ES cell to obtain a mutant mouse ES cell whose genome comprises a mutation in an endogenous mouse Col27a1 gene, wherein the mutation consists of a change of the codon encoding Gly at amino acid position 682 in the mouse Col27a protein to a codon encoding Arg; and
   (b) making a Col27a1 mutant mouse using the mutant mouse ES cell of (a).

6. A targeting nucleic acid construct, comprising
   a nucleic acid sequence to be integrated into a mouse Col27A1 gene at an endogenous mouse Col27a1 locus, flanked by a 5' nucleotide sequence and a 3' nucleotide sequence that are homologous to nucleotide sequences at the mouse Col27A1 locus, wherein integration of the nucleic acid sequence into the mouse Col27a1 gene results in a mutation in the endogenous mouse Col27a1 gene, wherein the mutation consists of a change of the codon encoding Gly at amino acid position 682 in the mouse Col27a protein to a codon encoding Arg.

7. A method of identifying a therapeutic agent for the treatment of Steel Syndrome, the method comprising
   (a) administering an agent to the mouse of claim 2;
   (b) performing one or more assays to determine if the agent has an effect on one or more abnormalities associated with Steel Syndrome; and
   (c) identifying the agent as a therapeutic agent when the agent has a therapeutic effect on the one or more abnormalities associated with Steel Syndrome.

8. The method of claim 7, wherein the agent is administered to the mouse at or shortly after birth.

9. The mouse of claim 1, wherein the mouse is a mix of a C57BL/6 strain and a 129 strain.

10. The mouse of claim 2, wherein the mouse is a mix of a C57BL/6 strain and a 129 strain.

11. The method of claim 5, wherein the mutant mouse made is a mix of a C57BL/6 strain and a 129 strain.

12. The method of claim 5, wherein the mutant mouse made is homozygous for the mutation in the endogenous mouse Col27a1 gene.

13. The method of claim 12, wherein the mutant mouse made is a mix of a C57BL/6 strain and a 129 strain.

* * * * *

SEQUENCE LISTING

<160> NUMBER OF SEQ ID NOS: 6

<210> SEQ ID NO 1
<211> LENGTH: 7818
<212> TYPE: DNA
<213> ORGANISM: Homo sapiens

<400> SEQUENCE: 1

| | | | | | |
|---|---|---|---|---|---|
| tctcctcccc | caggccggcg | gggaggcagc | ttccaccgcc | ctccgcgcgc | cctcacccgg | 60 |
| ccttgctctg | cctccgggga | ccgccagcag | cccgcctcca | aaagtttgat | catctctctc | 120 |
| tctcttttc | ttgcttcttc | ttccttttg | gtggaagcag | aaaaggaccg | aggcaggggc | 180 |
| gagcgcggcg | cccggactcc | tgggaccatg | ggcctggcgc | gggcgcccgc | ggggccccag | 240 |
| ccgcgctgcc | tgcctgctcg | ggcgcccctg | ggcgcggggc | tgcgctgggg | gcgcggggc | 300 |
| cgcgcgctct | aagccggcct | ggcgcggcgg | ggcgggggc | tggcggcccc | atggggcgcg | 360 |
| cccacacttg | cccccggc | tcgggagcat | gaagtagggg | cctgccatgg | gagcgggatc | 420 |
| ggcgcgggg | gcccgaggca | cagcggcggc | ggcggcggcg | cgcggggggg | ggtttctctt | 480 |
| ctcctggatc | ttagtctcgt | ttgcctgtca | cctggcctcc | acccaaggag | ctcctgaaga | 540 |
| tgtggacatc | ctccagcggc | tgggcctcag | ctggacgaag | gccgggagcc | ctgcaccccc | 600 |
| gggagtcatt | cctttccagt | cgggcttcat | ctttacgcag | cgggcccggc | tccaggctcc | 660 |
| cacgggcacc | gtcattcctg | ccgccttggg | cacagagctg | gcactggtgc | tgagcctctg | 720 |
| ctcccaccgg | gtgaaccatg | ccttcctctt | cgctgtccgc | agccagaaac | gcaagctgca | 780 |
| gctgggcctg | cagttcctcc | ccggcaagac | ggtcgtccac | ctcgggtccc | ggcgctcagt | 840 |
| ggccttcgac | ctcgacatgc | acgacgggcg | ctggcaccac | ctggccctcg | agctccgagg | 900 |
| ccgcacagtc | actctggtga | ctgcctgcgg | gcagcgccgg | gtgcctgtcc | tgctgccttt | 960 |
| ccacaggac | cctgcactcg | accctgggg | ctccttcctc | tttgggaaga | tgaacccgca | 1020 |
| tgcagtccag | tttgaaggtg | ctctctgcca | gttcagtatc | taccctgtga | cgcaggtcgc | 1080 |
| tcacaattac | tgtacccacc | tgaggaagca | gtgtggacag | gctgacacgt | accagtcccc | 1140 |
| actgggacct | ctcttctccc | aagactctgg | cagaccttt | accttccagt | ccgacctcgc | 1200 |
| cctgctaggc | ctggagaact | tgaccactgc | cacaccagcc | ctggggtcac | tgccagcagg | 1260 |
| caggggaccc | aggggactg | tggcacccgc | cacgcccacc | aagccccaaa | ggactagccc | 1320 |
| cacaaaccct | caccagcata | tggcggtggg | aggcccagcc | caaaccccgc | tgctacctgc | 1380 |
| caagctgtca | gccagtaacg | cacttgatcc | catgctccca | gcctctgttg | gcggctctac | 1440 |
| cagaacgcct | cgccctgcgg | ccgctcaacc | atcacagaag | atcacagcca | ccaaaatccc | 1500 |
| caaaagcctc | cctaccaagc | cttcggcccc | ttctacttca | attgtgccca | tcaaaagccc | 1560 |
| ccatcctacc | cagaaaacag | ctccatcttc | atttacaaag | tcagccctac | ccactcagaa | 1620 |
| gcaagtgcca | cctacttccc | gtccagttcc | tgccagagtc | tcccgtcccg | cagagaagcc | 1680 |
| catccagagg | aacccgggaa | tgccaggcc | ccaccgccc | agcacccggc | cctacctcc | 1740 |
| taccaccagc | tcctctaaaa | aacccattcc | cacactagct | cggactgagg | ccaagataac | 1800 |
| cagccatgcc | agtaagccgg | cctctgcccg | caccagcacc | cacaaacctc | ccccatttac | 1860 |
| tgctttatcc | tcatctcctg | cccctactcc | tggttctacc | aggagtactc | ggccaccagc | 1920 |
| cacgatggta | cctccaactt | cgggcaccag | cactcccaga | acagcacctg | ccgtccccac | 1980 |
| tcctggctca | gctcccactg | gaagcaagaa | gccattgga | tcggaagcct | caaagaaagc | 2040 |
| cggacccaag | agcagccccc | ggaagcctgt | ccccctcaga | cctgggaagg | cagccaggga | 2100 |

```
tgtcccctt g agcgatctga caaccaggcc tagccccaga cagccccagc ccagtcagca    2160
gaccaccccg gccctggtat tggccccggc gcaattcctg tcctccagcc cccggcccac    2220
gagcagtggc tattcgatct tccacctggc aggatctacg cctttccctc tgctgatggg    2280
gcctcccgga cccaagggag actgtggctt gccgggtccc cctgggctac ctgggctacc    2340
tggaatccct ggtgcacgtg ggcctcgggg tcctcctggg ccttatggaa atccaggtct    2400
ccccggcccc cctggagcca aggacagaa aggggaccca gggctctcac caggaaaggc    2460
ccacgatggg gcaaagggtg acatgggctt gcctgggctc tccgggaatc caggacctcc    2520
gggacgaaag ggacacaagg gctatcctgg accggcaggg caccccggag aacaggggca    2580
gccaggacct gagggcagcc caggggccaa aggttaccct ggcaggcagg ggttacctgg    2640
accggtagga gatcccggcc ccaaaggcag caggggctac attgggctcc cagggctctt    2700
cggcctgcca gggtctgatg gagaacgagg cctgcctggc gttcctggca gaggggcaa    2760 gatgggtatg ccggggtttc ctggagtctt tggggaaaga ggccctcctg gactggatgg    2820
aaatcctgga gaactgggcc tgccaggccc cctggagtc cccggcctca ttggtgactt    2880
aggagtgttg ggtccgattg gctacccggg acccaagggc atgaagggac tgatgggcag    2940
cgtgggggag cccggactga aggtgataa gggtgaacaa ggggttccag gtgtgtcagg    3000
agatcccgga ttccaaggag acaaggggag ccagggggttg ccagggttcc ccggtgcacg    3060
ggggaagcca gggcctctgg gcaaagtcgg agacaaagga tccattgggt ttcccgggcc    3120
ccctggaccc gagggattcc caggagacat cggcccccct ggcgacaatg cccagaagg    3180 catgaagggt aagcctggag cccgaggcct gccgggaccc cgtgggcagc tggggcccga    3240
gggagatgag ggacccatgg ggccgccagg ggccccctggc ttggagggtc agcctggcag    3300
gaagggtttt cctgggaggc ccggcctgga tggcgtgaag ggggaaccag gggatcctgg    3360
tcggccgggg cctgtgggag agcagggatt tatgggattc attggtctgg tcggggagcc    3420
aggaatcgtg ggagaaaagg gtgatcgtgg catgatggga ccccaggcg tgcctggacc    3480 caagggtcg atgggtcatc ctggaatgcc aggtggtatg gggaccccctg gagagcctgg    3540 accccagggt cctccaggat ctcgaggccc accaggcatg aggggagcaa agggacgtcg    3600
gggcccccga ggaccggacg gaccagctgg ggagcaaggg tccaggggcc tgaagggccc    3660
tccaggaccc cagggcagac cgggccggcc tggacagcag ggtgtggctg gtgagcgagg    3720
ccacttgggc tcgagaggct ttcctggcat cccgggtccc tcaggccccc caggcaccaa    3780
gggcctccca ggagaaccgg gccctcaggg accccagggg ccaattgggc ctccaggaga    3840
gatgggaccc aaggggccgc ctggtgcagt gggagaaccg ggccttcctg gggaagccgg    3900
gatgaagggt gaccttggac ccctgggcac tcctggggag cagggcctca ttgggcaacg    3960
gggagagcca ggccttgagg gtgacagtgg ccccatggga cctgatgggc tgaaggggga    4020
caggggagac ccaggcctg atggagaaca tggcagaaa ggcaggaag gctgatggg    4080 tgaggacggg ccccccggcc ccctggcgt cactggtgtc cggggtcctg aaggaaaatc    4140
agggaagcaa ggcgagaagg gccgcactgg agccaagggt gccaagggct atcaaggaca    4200
gctgggtgag atgggcgtcc ctggagaccc tggacccccct ggcactccag gccctaaagg    4260
gtcccggggc agcctgggac caacgggtgc tccgggacgc atgggggccc aaggagaacc    4320
gggactggct ggttatgatg gacacaaagg cattgtggga cccttggac ctcctggacc    4380 aaaaggcgaa aaggggagc agggcgagga cggcaaggct gaggggccccc ctgggccacc    4440
```

```
tggagatcgg ggccctgtgg gtgatcgagg agaccgcggg gaaccgggag accctgggta   4500
ccctggacag gagggtgtgc aaggcctccg tggaaagcca ggccagcagg gccaacccgg   4560
gcatccggga ccccgggggt ggccgggacc caaaggatcg aaaggcgcag agggaccaaa   4620
gggaaagcaa ggcaaggcag gggcccagg ccggaggggg gtccagggcc tgcaggggct    4680
gccagggccc cggggcgtgg tggggagaca gggcctcgag ggcatcgctg gaccagatgg   4740
gcttcctggc agggacgggc aagcaggaca gcagggggag cagggagacg atggggaccc   4800
tggccccatg ggccctgctg ggaagagagg aaatccaggt gtggccggct tacctggagc   4860
acagggaccc ccaggattca aggtgagag tgggttaccc ggacagctgg gtcccctgg    4920
caagcgagga acagagggca gaacggggct ccctggaaac caggggagc ctgggtccaa    4980
aggccagccg ggcgactctg gcgagatggg cttcccagga atggcaggtc tcttcggacc   5040
caagggcccg cctggagaca ttggcttcaa aggcatccag ggccctcggg ggccacctgg   5100
cttgatggga aaggaaggca tcgtcgggcc cctcggaatc ctgggacctt cgggactccc   5160
gggtccgaag ggtgacaaag gcagccgtgg ggactgggga ttgcaaggtc cgagggtcc   5220
tcccggcccc agagggcggc ccggcccccc gggtcctcca ggggtcccta tccaattgca   5280
acaagatgat cttggggcag cttttccgac gtggatggac accagtggag cactcaggcc   5340
agagagttac agctatccag accggctggt gctggaccag ggaggagaga tctttaaaac   5400
cttacactac ctcagcaacc tcatccagag cattaagacg cccctgggca ccaaagagaa   5460
ccccgcccgg gtctgcaggg acctcatgga ctgtgagcag aagatggtgg atggtaccta   5520
ctgggtggat ccaaaccttg gctgctcctc tgacaccatc gaggtctcct gcaacttcac   5580
tcatggtgga cagacgtgtc tcaagcccat cacggcctcc aaggtcgagt ttgccatcag   5640
ccgggtccga atgaatttcc tgcacctgct aagctccgag gtgacccagc acatcaccat   5700
ccactgcctt aacatgaccg tgtggcagga gggcactggg cagaccccag ccaagcaggc   5760
cgtacgcttc cgggcctgga atggacagat ttttgaagct ggggtcagt tccgcccga    5820
ggtgtccatg gatggctgca aggtccaaga tggccgctgg catcagacac tcttcacctt   5880
ccggacccaa gaccccaac agctgccat catcagtgtg gacaacctcc ctcctgcctc    5940
atcagggaag cagtaccgcc tggaagttgg acctgcgtgc ttcctctgac ctctgacctc   6000
gtggccactc taggcctcac ggaggaggga agaggaagag gcaagggag ggtactgagg    6060
ggcagatggc tccaggagag gcagctcccc tgcccaaggg tccttgggca gaccccagct   6120
gttgtctgcc cagtagaagt gggtgggggt aggaggggat agggtgtcct tgggaacaat   6180
ggatcccagc ttagccccaa agaccaacca aagagccagc cagagtaagc tggacctgca   6240
acctgcctga gccccgtggc ctctcagctc tgcggcacc ccgttccctc cccagcttcc    6300
tgcccaaaga gccccacatt caagccaact tgagggaagg gggcgtctcg tcagctggtc   6360
cctgctaggg agctattgat gtgcaatatt agaaaggaga catgaaaaaa ggagaaaagg   6420
aaagacagaa gtgtatatat atattattta aacaaacaaa agaaggtgc gttactattt    6480
tttttttcacc cggaaagag gtgagaggat gggaaggagc agccaggcgt gggaagcggc   6540
gagatcctcg ggctggggt gcccacgttt gctacctccc actgtgaaat cgctggtgct    6600
cacaattgtc tctcacagtg tatgtgattt ttttaaggaa aaaaaaaat ccctatttaa    6660
gattctgaag gtgctaccat tattttgcca cagactttga agaaactttt ggatgtgggg   6720
catcatccga atctttctct ctcctccaaa tgacaaagtt tggggaattt ttgaattttc    6780
ctagcatcgc ccttgtgctc atcaggtaat ctgctaagga ggaaaaaaga aagaaaaaa    6840
```

-continued

```
ggaaaaaaaa aaaaaaaaag caaaacaaaa acaaaaacaa aaaccctacc agaaaccaga      6900
agtagagaga tttaccatat aacttatgga ctttgaaatg tctgtccttt taaggcagca      6960
gggaggcctg ggtgcgaagc atgttggctt ggcccttcac ggtcctggag ggaggtgagg      7020
ctggccttgg aaggcgtgcc ctggagaggt cttgggtgaa aacttgacct tgaagaaacc      7080
aatcacaaaa gcggcgttgg gtcagggcta ggcttagagg tgaagcatca acatggaacc      7140
atctcaggaa gccgcatcgc ctcttccgag gtcctcactt ccaggagcct gtccttgcaa      7200
gatgcaatca tcgttcctgc ttttcattg tcattaaatt ctgtagaaac ccattgtcat       7260
tagctccaag tgtaaatttg ggtcaaggag acagaataat aatgggaatc tcggagttcg      7320
acaccatagt gacgttcagc gtcctctgaa ttgtgctaca tcagcgaaca agtcggcgct      7380
tgaattggat tttgaggtta ttttaaccat ggaattattt ttatagaagg ggaaaatgta      7440
tgtgaaagtc tctatttgtg tatttctctc ctaaagttgt gtctctttgg gaattggatt      7500
tgatttttat tatttaatac ctcactttgg cccgtccccc ctcccaacac ttctgtatcc      7560
tcgccctgcc gccccagcct ggacgctctg cgtggaagtg cgtgtttgta gcagctcggg      7620
cctcatctca gcgctcggat ccctcctgct gccagaatcc actggcctct gtctcattct      7680
tgggttttcc tgctgtcttc gtttacgtct ctgtccacat gtcagtgtat taaaacccca      7740
atgggttccg tttctccttt tccctctgg attttaaata aatatttaaa actgaggcaa       7800
tggaatgaca aaaaaaaa                                                    7818
```

<210> SEQ ID NO 2
<211> LENGTH: 1860
<212> TYPE: PRT
<213> ORGANISM: Homo sapiens

<400> SEQUENCE: 2

```
Met Gly Ala Gly Ser Ala Arg Gly Ala Arg Gly Thr Ala Ala Ala Ala
1               5                   10                  15

Ala Ala Arg Gly Gly Gly Phe Leu Phe Ser Trp Ile Leu Val Ser Phe
            20                  25                  30

Ala Cys His Leu Ala Ser Thr Gln Gly Ala Pro Glu Asp Val Asp Ile
        35                  40                  45

Leu Gln Arg Leu Gly Leu Ser Trp Thr Lys Ala Gly Ser Pro Ala Pro
    50                  55                  60

Pro Gly Val Ile Pro Phe Gln Ser Gly Phe Ile Phe Thr Gln Arg Ala
65                  70                  75                  80

Arg Leu Gln Ala Pro Thr Gly Thr Val Ile Pro Ala Ala Leu Gly Thr
                85                  90                  95

Glu Leu Ala Leu Val Leu Ser Leu Cys Ser His Arg Val Asn His Ala
            100                 105                 110

Phe Leu Phe Ala Val Arg Ser Gln Lys Arg Lys Leu Gln Leu Gly Leu
        115                 120                 125

Gln Phe Leu Pro Gly Lys Thr Val Val His Leu Gly Ser Arg Arg Ser
    130                 135                 140

Val Ala Phe Asp Leu Asp Met His Asp Gly Arg Trp His His Leu Ala
145                 150                 155                 160

Leu Glu Leu Arg Gly Arg Thr Val Thr Leu Val Thr Ala Cys Gly Gln
                165                 170                 175

Arg Arg Val Pro Val Leu Leu Pro Phe His Arg Asp Pro Ala Leu Asp
            180                 185                 190
```

```
Pro Gly Gly Ser Phe Leu Phe Gly Lys Met Asn Pro His Ala Val Gln
            195                 200                 205
Phe Glu Gly Ala Leu Cys Gln Phe Ser Ile Tyr Pro Val Thr Gln Val
    210                 215                 220
Ala His Asn Tyr Cys Thr His Leu Arg Lys Gln Cys Gly Gln Ala Asp
225                 230                 235                 240
Thr Tyr Gln Ser Pro Leu Gly Pro Leu Phe Ser Gln Asp Ser Gly Arg
                245                 250                 255
Pro Phe Thr Phe Gln Ser Asp Leu Ala Leu Leu Gly Leu Glu Asn Leu
            260                 265                 270
Thr Thr Ala Thr Pro Ala Leu Gly Ser Leu Pro Ala Gly Arg Gly Pro
            275                 280                 285
Arg Gly Thr Val Ala Pro Ala Thr Pro Thr Lys Pro Gln Arg Thr Ser
    290                 295                 300
Pro Thr Asn Pro His Gln His Met Ala Val Gly Gly Pro Ala Gln Thr
305                 310                 315                 320
Pro Leu Leu Pro Ala Lys Leu Ser Ala Ser Asn Ala Leu Asp Pro Met
                325                 330                 335
Leu Pro Ala Ser Val Gly Gly Ser Thr Arg Thr Pro Arg Pro Ala Ala
            340                 345                 350
Ala Gln Pro Ser Gln Lys Ile Thr Ala Thr Lys Ile Pro Lys Ser Leu
    355                 360                 365
Pro Thr Lys Pro Ser Ala Pro Ser Thr Ser Ile Val Pro Ile Lys Ser
    370                 375                 380
Pro His Pro Thr Gln Lys Thr Ala Pro Ser Ser Phe Thr Lys Ser Ala
385                 390                 395                 400
Leu Pro Thr Gln Lys Gln Val Pro Pro Thr Ser Arg Pro Val Pro Ala
                405                 410                 415
Arg Val Ser Arg Pro Ala Glu Lys Pro Ile Gln Arg Asn Pro Gly Met
            420                 425                 430
Pro Arg Pro Pro Pro Ser Thr Arg Pro Leu Pro Pro Thr Thr Ser
    435                 440                 445
Ser Ser Lys Lys Pro Ile Pro Thr Leu Ala Arg Thr Glu Ala Lys Ile
450                 455                 460
Thr Ser His Ala Ser Lys Pro Ala Ser Ala Arg Thr Ser Thr His Lys
465                 470                 475                 480
Pro Pro Pro Phe Thr Ala Leu Ser Ser Pro Ala Pro Thr Pro Gly
                485                 490                 495
Ser Thr Arg Ser Thr Arg Pro Ala Thr Met Val Pro Pro Thr Ser
            500                 505                 510
Gly Thr Ser Thr Pro Arg Thr Ala Pro Ala Val Pro Thr Pro Gly Ser
            515                 520                 525
Ala Pro Thr Gly Ser Lys Lys Pro Ile Gly Ser Glu Ala Ser Lys Lys
    530                 535                 540
Ala Gly Pro Lys Ser Ser Pro Arg Lys Pro Val Pro Leu Arg Pro Gly
545                 550                 555                 560
Lys Ala Ala Arg Asp Val Pro Leu Ser Asp Leu Thr Arg Pro Ser
                565                 570                 575
Pro Arg Gln Pro Gln Pro Ser Gln Gln Thr Thr Pro Ala Leu Val Leu
            580                 585                 590
Ala Pro Ala Gln Phe Leu Ser Ser Pro Arg Pro Thr Ser Ser Gly
    595                 600                 605
Tyr Ser Ile Phe His Leu Ala Gly Ser Thr Pro Phe Pro Leu Leu Met
```

```
            610                 615                 620
Gly Pro Pro Gly Pro Lys Gly Asp Cys Gly Leu Pro Gly Pro Pro Gly
625                 630                 635                 640

Leu Pro Gly Leu Pro Gly Ile Pro Gly Ala Arg Gly Pro Arg Gly Pro
                645                 650                 655

Pro Gly Pro Tyr Gly Asn Pro Gly Leu Pro Gly Pro Pro Gly Ala Lys
                660                 665                 670

Gly Gln Lys Gly Asp Pro Gly Leu Ser Pro Gly Lys Ala His Asp Gly
                675                 680                 685

Ala Lys Gly Asp Met Gly Leu Pro Gly Leu Ser Gly Asn Pro Gly Pro
690                 695                 700

Pro Gly Arg Lys Gly His Lys Gly Tyr Pro Gly Pro Ala Gly His Pro
705                 710                 715                 720

Gly Glu Gln Gly Gln Pro Gly Pro Glu Gly Ser Pro Gly Ala Lys Gly
                725                 730                 735

Tyr Pro Gly Arg Gln Gly Leu Pro Gly Val Gly Asp Pro Gly Pro
                740                 745                 750

Lys Gly Ser Arg Gly Tyr Ile Gly Leu Pro Gly Leu Phe Gly Leu Pro
                755                 760                 765

Gly Ser Asp Gly Glu Arg Gly Leu Pro Gly Val Pro Gly Lys Arg Gly
770                 775                 780

Lys Met Gly Met Pro Gly Phe Pro Gly Val Phe Gly Glu Arg Gly Pro
785                 790                 795                 800

Pro Gly Leu Asp Gly Asn Pro Gly Glu Leu Gly Leu Pro Gly Pro Pro
                805                 810                 815

Gly Val Pro Gly Leu Ile Gly Asp Leu Gly Val Leu Gly Pro Ile Gly
                820                 825                 830

Tyr Pro Gly Pro Lys Gly Met Lys Gly Leu Met Gly Ser Val Gly Glu
                835                 840                 845

Pro Gly Leu Lys Gly Asp Lys Gly Glu Gln Gly Val Pro Gly Val Ser
                850                 855                 860

Gly Asp Pro Gly Phe Gln Gly Asp Lys Gly Ser Gln Gly Leu Pro Gly
865                 870                 875                 880

Phe Pro Gly Ala Arg Gly Lys Pro Gly Pro Leu Gly Lys Val Gly Asp
                885                 890                 895

Lys Gly Ser Ile Gly Phe Pro Gly Pro Pro Gly Glu Gly Phe Pro
                900                 905                 910

Gly Asp Ile Gly Pro Pro Gly Asp Asn Gly Pro Glu Gly Met Lys Gly
                915                 920                 925

Lys Pro Gly Ala Arg Gly Leu Pro Gly Pro Arg Gly Gln Leu Gly Pro
930                 935                 940

Glu Gly Asp Glu Gly Pro Met Gly Pro Pro Gly Ala Pro Gly Leu Glu
945                 950                 955                 960

Gly Gln Pro Gly Arg Lys Gly Phe Pro Gly Arg Pro Gly Leu Asp Gly
                965                 970                 975

Val Lys Gly Glu Pro Gly Asp Pro Gly Arg Pro Gly Pro Val Gly Glu
                980                 985                 990

Gln Gly Phe Met Gly Phe Ile Gly  Leu Val Gly Glu Pro  Gly Ile Val
                995                 1000                1005

Gly Glu  Lys Gly Asp Arg Gly  Met Met Gly Pro Pro  Gly Val Pro
    1010                1015                1020

Gly Pro  Lys Gly Ser Met Gly  His Pro Gly Met Pro  Gly Gly Met
    1025                1030                1035
```

-continued

Gly Thr Pro Gly Glu Pro Gly Pro Gln Gly Pro Pro Gly Ser Arg
    1040                1045                1050

Gly Pro Pro Gly Met Arg Gly Ala Lys Gly Arg Arg Gly Pro Arg
    1055                1060                1065

Gly Pro Asp Gly Pro Ala Gly Glu Gln Gly Ser Arg Gly Leu Lys
    1070                1075                1080

Gly Pro Pro Gly Pro Gln Gly Arg Pro Gly Arg Pro Gly Gln Gln
    1085                1090                1095

Gly Val Ala Gly Glu Arg Gly His Leu Gly Ser Arg Gly Phe Pro
    1100                1105                1110

Gly Ile Pro Gly Pro Ser Gly Pro Pro Gly Thr Lys Gly Leu Pro
    1115                1120                1125

Gly Glu Pro Gly Pro Gln Gly Pro Gln Gly Pro Ile Gly Pro Pro
    1130                1135                1140

Gly Glu Met Gly Pro Lys Gly Pro Pro Gly Ala Val Gly Glu Pro
    1145                1150                1155

Gly Leu Pro Gly Glu Ala Gly Met Lys Gly Asp Leu Gly Pro Leu
    1160                1165                1170

Gly Thr Pro Gly Glu Gln Gly Leu Ile Gly Gln Arg Gly Glu Pro
    1175                1180                1185

Gly Leu Glu Gly Asp Ser Gly Pro Met Gly Pro Asp Gly Leu Lys
    1190                1195                1200

Gly Asp Arg Gly Asp Pro Gly Pro Asp Gly Glu His Gly Glu Lys
    1205                1210                1215

Gly Gln Glu Gly Leu Met Gly Glu Asp Gly Pro Pro Gly Pro Pro
    1220                1225                1230

Gly Val Thr Gly Val Arg Gly Pro Glu Gly Lys Ser Gly Lys Gln
    1235                1240                1245

Gly Glu Lys Gly Arg Thr Gly Ala Lys Gly Ala Lys Gly Tyr Gln
    1250                1255                1260

Gly Gln Leu Gly Glu Met Gly Val Pro Gly Asp Pro Gly Pro Pro
    1265                1270                1275

Gly Thr Pro Gly Pro Lys Gly Ser Arg Gly Ser Leu Gly Pro Thr
    1280                1285                1290

Gly Ala Pro Gly Arg Met Gly Ala Gln Gly Glu Pro Gly Leu Ala
    1295                1300                1305

Gly Tyr Asp Gly His Lys Gly Ile Val Gly Pro Leu Gly Pro Pro
    1310                1315                1320

Gly Pro Lys Gly Glu Lys Gly Glu Gln Gly Glu Asp Gly Lys Ala
    1325                1330                1335

Glu Gly Pro Pro Gly Pro Pro Gly Asp Arg Gly Pro Val Gly Asp
    1340                1345                1350

Arg Gly Asp Arg Gly Glu Pro Gly Asp Pro Gly Tyr Pro Gly Gln
    1355                1360                1365

Glu Gly Val Gln Gly Leu Arg Gly Lys Pro Gly Gln Gln Gly Gln
    1370                1375                1380

Pro Gly His Pro Gly Pro Arg Gly Trp Pro Gly Pro Lys Gly Ser
    1385                1390                1395

Lys Gly Ala Glu Gly Pro Lys Gly Lys Gln Gly Lys Ala Gly Ala
    1400                1405                1410

Pro Gly Arg Arg Gly Val Gln Gly Leu Gln Gly Leu Pro Gly Pro
    1415                1420                1425

-continued

```
Arg Gly Val Val Gly Arg Gln Gly Leu Glu Gly Ile Ala Gly Pro
    1430                1435                1440
Asp Gly Leu Pro Gly Arg Asp Gly Gln Ala Gly Gln Gln Gly Glu
    1445                1450                1455
Gln Gly Asp Asp Gly Asp Pro Gly Pro Met Gly Pro Ala Gly Lys
    1460                1465                1470
Arg Gly Asn Pro Gly Val Ala Gly Leu Pro Gly Ala Gln Gly Pro
    1475                1480                1485
Pro Gly Phe Lys Gly Glu Ser Gly Leu Pro Gly Gln Leu Gly Pro
    1490                1495                1500
Pro Gly Lys Arg Gly Thr Glu Gly Arg Thr Gly Leu Pro Gly Asn
    1505                1510                1515
Gln Gly Glu Pro Gly Ser Lys Gly Gln Pro Gly Asp Ser Gly Glu
    1520                1525                1530
Met Gly Phe Pro Gly Met Ala Gly Leu Phe Gly Lys Gly Pro
    1535                1540                1545
Pro Gly Asp Ile Gly Phe Lys Gly Ile Gln Gly Pro Arg Gly Pro
    1550                1555                1560
Pro Gly Leu Met Gly Lys Glu Gly Ile Val Gly Pro Leu Gly Ile
    1565                1570                1575
Leu Gly Pro Ser Gly Leu Pro Gly Pro Lys Gly Asp Lys Gly Ser
    1580                1585                1590
Arg Gly Asp Trp Gly Leu Gln Gly Pro Arg Gly Pro Pro Gly Pro
    1595                1600                1605
Arg Gly Arg Pro Gly Pro Pro Gly Pro Pro Gly Gly Pro Ile Gln
    1610                1615                1620
Leu Gln Gln Asp Asp Leu Gly Ala Ala Phe Gln Thr Trp Met Asp
    1625                1630                1635
Thr Ser Gly Ala Leu Arg Pro Glu Ser Tyr Ser Tyr Pro Asp Arg
    1640                1645                1650
Leu Val Leu Asp Gln Gly Gly Glu Ile Phe Lys Thr Leu His Tyr
    1655                1660                1665
Leu Ser Asn Leu Ile Gln Ser Ile Lys Thr Pro Leu Gly Thr Lys
    1670                1675                1680
Glu Asn Pro Ala Arg Val Cys Arg Asp Leu Met Asp Cys Glu Gln
    1685                1690                1695
Lys Met Val Asp Gly Thr Tyr Trp Val Asp Pro Asn Leu Gly Cys
    1700                1705                1710
Ser Ser Asp Thr Ile Glu Val Ser Cys Asn Phe Thr His Gly Gly
    1715                1720                1725
Gln Thr Cys Leu Lys Pro Ile Thr Ala Ser Lys Val Glu Phe Ala
    1730                1735                1740
Ile Ser Arg Val Gln Met Asn Phe Leu His Leu Leu Ser Ser Glu
    1745                1750                1755
Val Thr Gln His Ile Thr Ile His Cys Leu Asn Met Thr Val Trp
    1760                1765                1770
Gln Glu Gly Thr Gly Gln Thr Pro Ala Lys Gln Ala Val Arg Phe
    1775                1780                1785
Arg Ala Trp Asn Gly Gln Ile Phe Glu Ala Gly Gly Gln Phe Arg
    1790                1795                1800
Pro Glu Val Ser Met Asp Gly Cys Lys Val Gln Asp Gly Arg Trp
    1805                1810                1815
His Gln Thr Leu Phe Thr Phe Arg Thr Gln Asp Pro Gln Gln Leu
```

-continued

```
                1820                1825                1830
Pro Ile Ile Ser Val Asp Asn Leu Pro Pro Ala Ser Ser Gly Lys
        1835                1840                1845
Gln Tyr Arg Leu Glu Val Gly Pro Ala Cys Phe Leu
    1850                1855                1860

<210> SEQ ID NO 3
<211> LENGTH: 7635
<212> TYPE: DNA
<213> ORGANISM: Mus musculus

<400> SEQUENCE: 3
ccttttcctc tcctccccca ggccggcggg gaggcagctt ccaccgccct ccgcgcgcgc      60
tctcccggcc ttgctctgcc tccagagacc gctagcggcc cgcctccaaa agtttgatca     120
tctctctctc cctgcctttt cttgcttctt ccttttcggt ggaagcagaa aaagagcgag     180 gcagggcga gcgcggctcc ggcagtcctg ggaccatggg cctggcgcgg gcgaccgccg     240
ggctggggcc gtgctgtccg tctgctccgg cgccctggg gcaggactg gctgggggt     300 gcgccggcag cgcgctttga ccggcctgg cgcggcgcgg cggggggctg gcggccccat     360
ggggcgcgcc cacacttgcc ccccgggctc cgcagcatga agtaggggcc tgccatgggc     420
acgggattcg cgcggggggc ccgaggcaca gcggcgtcag gacccgggg ggggtttctc     480 ttcgcctgga tcttggtctc atttacctgt cacctggcct ccacccaagg agctcctgaa     540
gatgtggatg tcctccagcg ctgggcctc agctggacga aggccggggg tggccggagt     600
cctacacccc ctggtgtcat tcctttccca tctggcttca tcttcacaca gcgggccaag     660
ctgcaggccc ccacagccaa tgttcttccc accaccctgg ggcgggagct ggcattggtg     720
ttgagcctct gttcacatcg tgtgaaccat gccttcctct tgccatccg cagcaggaaa     780 cacaagctgc aactgggtct gcagttcctc cccggcagga cgatcatcca cctggggcct     840
cggcaatcag tggccttcga cttggatgtg catgatgggc gctggcacca cctgccta     900 gagttgcgtg gccgcacagt cacaatggtg acagcctgtg ggcagcacag ggtacctgtc     960
ccactgcctt cccgtaggga ctccatgctt gacccccagg gctcctttct cttggggaag    1020
gtgaaccccc gtgctgtcca gtttgaaggt gcactctgtc agttcagcat ccaccctgtg    1080
gcgcaggtcg ctcacaatta ctgtgcccac ctgagagagc ggtgccgaca ggtgacaca    1140 tatagtcccc aggtgggaac cctctttcct tgggactctg gcccagcctt tgctttgcat    1200
cctgaaccag ccttgcttgg cttggggaat ctgaccagaa ctccagcaac cctgggggcc    1260
aggcctgtaa gcagggcact tgcagtgact ctggctcctg ccatgcccac caagcccctg    1320
aggactgtcc acccagatgt ctctgaacac agctcttccc agaccccact gtcacctgcc    1380
aaacagtcgg ccaggaaaac accttccccc tcctcgtcag cttccctggc taattccacc    1440
agggtttatc gtccagctgc tgcccagcca agacagatca caactactag ccccaccaaa    1500 cgttcccca ccaagccttc tgtttctccc ctttcagtta ccccatgaa aagtcccat    1560 gcaacccaga aaacaggtgt cccttcattc acaaagcctg ttccacccac tcagaagcca    1620
gcgcccttca cctcctacct agcaccttcc aaagcctcta gtcccactgt gaggcctgtt    1680
cagaagactt tcatgacacc ccgacctcca gtccccagcc cccagcccct cgcgccctact    1740 actggcttat ctaagaagtt cactaacccc actgttgcaa aatctaagtc caagacgacc    1800
agttgggcca gcaagccggt cttggcccgc tccagtgtcc ctaaaacgct tcagcaaact    1860
gttttgtccc agtctcctgt ttcctatctg ggctctcaga cactggctcc agccctccct    1920
```

```
cctttgggtg ttggaaatcc tagaacgatg cctcccacac gtgactctgc tttaactcct    1980
gctggaagca agaaattcac aggacgggaa acctccaaga aaaccagaca gaagagcagc    2040
ccccggaagc ccgaacctct cagccctggg aagtcagcca gggatgcctc accaagagac    2100
ctgacaacca agcctagccg gccgtccacc ccagccctgg tccttgcccc agcttacctc    2160
ctgtcctcca gccccagcc caccagcagc agcttccctt tcttccacct gctgggccct     2220
acacctttcc cgatgctgat ggggcctcca ggctccaagg gagactgtgg cttgccgggt    2280 cccctgggc ttccaggatt acctggatct ccgggcgcac gaggtcctcg gggtcctcct     2340
gggccgtacg ggaacccagg cccacctggc cctccaggag ccaaaggaca gaaaggggac    2400
ccaggactct caccaggaca ggctcacgat ggagcaaagg caacatgggc ttgcctggg    2460 ctctccggaa atccaggacc cttgggaagg aagggacaca agggccatcc tggagcagca    2520
gggcaccctg gagaacaggg gcagccagga cctgagggca gtccaggggc caaaggttac    2580
cctggcaggc aggggttccc tggacctgta ggagaccctg gccccaaagg cagcaggggt    2640
tacattggtc ttccggggct ctttggcctg ccagggtcgg atggagagcg ggtctccct    2700 ggcgttcctg gcaagagggg cgagatgggt aggccgggct ccctggaga ctttggggaa    2760 agaggccccc ctggacttga tggcaaccct ggagaaattg gcctgccggg gccaccagga    2820
gtgctcgggc tcattggtga cacaggagca ctgggcccag ttggctaccc aggaccgaaa    2880
ggcatgaagg gactgatggg cggcgtgggg gagcccggac tgaaaggtga taagggtgaa    2940 caagggtgc caggtgtgtc gggagatcct ggcttccaag gagacaaggg gagtcatggc    3000
ttgccagggc tcccgggtgg ccgggggaag ccagggcctc tgggaaaagc tggagacaaa    3060
ggatcacttg ggtttcctgg acctcctgga cctgagggtt cccaggaga cattggccct    3120 ccaggggaca atggccctga aggcatgaag ggtaagcctg gagcccgagg cctgcctgga    3180
cctcctgggc agctggggcc tgagggagat gaaggaccca tggggccacc aggagtccca    3240
ggcttggagg gtcagcctgg aaggaaaggg tttcctggga ggcctggcct ggatggctcg    3300
aaggggaaac caggggatcc tggacggcca ggacctgtgg gtgaacaggg gcttatggga    3360
ttcattggtc ttgtcggaga gcctggaatt gttggggaga agggagaccg tggggtgatg    3420 ggaccccag gtgcacctgg acccaagggg tcgatgggcc atcctggaac cccggtggt    3480 attgggaacc ctggagagcc tggaccctgg gccctccag gatctcgagg cctgccaggc    3540
atgaggggag ccaaggggca ccggggccct cgaggacctg atggaccagc tggggagcag    3600
ggatccaagg gcctgaaggg tcgtgtagga cctcggggca gacctggcca gccaggacag    3660
cagggtgcag ctggtgagcg aggccactca ggtgcaaaag gcttccttgg catccctggt    3720
ccctcaggcc ctccaggtgc caaggcctc ccaggagaac cgggctctca gggacctcag     3780
gggccagttg gtcctccagg agaaatgggg cccaagggac cgccgggtgc agtgggagag    3840 cctgccttc ctggggactc cggaatgaag ggtgacctcg gacctctggg cccccctggg     3900
gagcaaggtc ttattgggca gcggggagag ccaggccttg agggagacca tggccctgtg    3960
gggccagatg ggctgaaggg cgacagggc gacccagggc ccgatggcga gcatggtgaa    4020
aagggccagg aagggctgaa aggagaggat gggtcccctg gccccccggg catcactggc    4080
gtcccgggtc gtgaggggaa gccgggcaag cagggtgaga aggccagag gggagctaag    4140 ggtgccaagg gccaccaagg atatctggga gagatgggca tccccggaga acctgggccc    4200
cctgggaccc caggtcctaa agggtcccgg ggcaccctag gaccaacggg tgctccagga    4260
```

```
cggatgggag cccaaggaga accaggattg gccggttata atggacacaa aggcatcaca   4320
ggacccctcg ggcctcccgg gcccaaaggc gagaaggggg accagggcga ggatggcaag   4380 accgagggc cccctgggcc accaggagat cggggtcctg tgggtgatcg aggagaccgt   4440
ggggagccag gcgaccctgg ataccctggt caagagggga ttcaaggcct ccgtggagaa   4500
ccgggccagc agggacagcc tgggcatcca ggaccccggg ggcgcccagg acccaaagga   4560
tcaaaaggcg aagagggccc aaagggaaag ccaggcaagg ctgggccatc aggccggagg   4620
gggacccagg gccttcaagg actgccaggc ccccgaggcg tggtggggag acagggccct   4680
gagggcactg ctggatctga tgggattcct ggcagagatg gtcggccagg atatcaggga   4740
gaccagggaa atgatgggga ccctggccct gtgggccctg ctgggagaag aggaaatcca   4800
ggtgtggctg gcttgcctgg agcacagggg cctccgggat tcaagggtga agtgggtta   4860 cctgggcaac tgggtccccc tggaaaacga gggacagaag gtgaacagg gcttcctggg   4920 aaccagggg agccaggatc caaaggccag ccgggtgact ctggcgagat gggcttccca   4980
ggagtggctg gcctctttgg acccaaggc ccccctggga cattggctt caaaggcatc   5040 caaggtcctc gggggcctcc tggcttgatg ggaaaggaag gtatcattgg ccccccgga   5100 atgctgggac cttctggact cccgggtccc aaaggtgaca gaggcagccg aggagacttg   5160
ggactgcaag gccaaggggg tcctcctggt ccaaggggcc ggccaggtcc ccgggccct   5220 ccttggcatc ccatccagtt tcagcaagat gaccttggag cagcttttcca gacatggatg   5280 gatgctcaag gagccgtcag atcggagggg tacagctatc cggaccagct ggcgctagac   5340
cagggagggg agatcttcaa aaccttacac tacctcagca acctcatcca gagcattaag   5400
acacccttgg gcaccaagga gaacccagcc cgggtctgcc gggacctcat ggactgtgag   5460
cagaggatgc cggatggtac ctactgggtg acccccaacc tcggctgctc ctctgacacc   5520
attgaagtct cctgcaactt tacacagggt gggcagacgt gcctgaagcc catcacggcc   5580
tccaaggccg agtttgctgt gagtcgggtc cagatgaatt tcttgcacct gctgagctct   5640
gaggggacac agcatatcac aatccactgt ctgaacatga cggtgtggca ggagggaccg   5700
ggacgctcct ctgccagaca ggctgtgcgc ttccgtgcct ggaacggaca ggtcttcgaa   5760
gctgggggtc agttcaggcc agaggtgtct atggatggct gcaaggtcca tgatggccgc   5820
tggcatcaga cactgttcac cttccggacc caggaccccc agcagctgcc catcgtcagt   5880
gtggacaatc tcccgcctgt ctcatcaggg aagcagtacc gcctggaagt tggacctgcg   5940
tgcttcctct gacctctgac ctctaggctc atctaagcct tgtggggaaa gggaagagat   6000
ggggacagct ggtcccagga gatgcaggcc cttgccttag gatcctggtg caggtcctag   6060
ttgttatctg ctcagccgga gttgagaagg agtaacaggt ctgaggctgt cccggagaac   6120
cacccatccc agctcagccc caagaaccaa ccaaagagcc agtcaaaagc aagctgggtt   6180
tgcagcccac tccagcccat ggcctgttgc ccagctctgt agacatccct gctccccagc   6240
tgcccaaaga cccctccccc attgatgcca cctcaaggaa agggggcatg ttgccagctg   6300
gttcccgcta gggagctttc gatgtgcaat attagaaagg acatggaa aaaaaaagag   6360 gaggaaaagg aaagaaatct atatatatta tttaaacaaa gagaaggtgt gttactattt   6420
ttttcacttg ggagaggtga ggaagagcaa gagaagctgg gggtgtggag aggcaggtcc   6480
cccaggctgg gatgctggcc ctagactag ggtgctgacc cctgggctgg ggtgctgtgt   6540
gctacctccc actgtgaaat cgctggtgct cacaattgtc tcttgtaatg tatgtgatttt   6600 ttttaaggag aaaaagaaac ttatttaaga ttctgaaggt gctactattt tctgttgcca   6660
```

-continued

```
caggctttaa agaaactttc tgaatggggc ctggcccact tctctttctc tcctccaaat      6720
gaggagttaa aaatgttact agcatagccc accegtgtaa tccgttgaaa aggaacaaaa      6780
ggaaaaaaga aagaaagaa agaaaaaaa aagaaaaaga aaaacaaaa caaaacaaaa        6840 aaatcctcct agaaaccaga agtagagaga tttctgctaa ttctgggctt tgaagcgtac      6900
gtcttttgag ggggcatttt gatgtggtcc tccttgcttc tggagggact tggttccctt     6960
tagaaaacct gccctgggaa aagacttctt ggttttgagg aagatccttg gttagcgatg     7020
atcttggagg tggactaagt ccagagccat ccctgaagcc aggtgactgt cccaaggtct     7080
tccctcccgg gagcccaacc tttcgagtgc agccaaacct tactgctttt acaacattgc     7140
acagctgtgt agaaaccccg tgttctttcc cataggtgcc aatttgggtg ggggaggaag    7200
gaacaattac aagatcccca tctgtctgcc catgccacct aaacaagtca ggactccaat    7260
tggattttga agttatttta attatagaat tattttttta gaagaaagat ggatgtgata    7320
gtctatattt gtgtgtttct aaagttgtgt cttgtggggg aattggattc cattttagtt   7380
atttaatacc tcactcccac ccacctgcat actgcttgtg tgtcccggcc tgtcccgcaa   7440
gcctagttgt gctttttgtt gtctgttccc cgtgccccct cctgtgtctc actctgtctt   7500
cttgtcactt gatgtgcatt tgctgttgtt ctttcgtttc tgtctaaatg tcagtgtgtt   7560
caaaccccca gagggttctg tttttcccat tccttctgg acttaaata aatatttaaa     7620 actgagcaat ggaaa                                                     7635
```

<210> SEQ ID NO 4
<211> LENGTH: 1845
<212> TYPE: PRT
<213> ORGANISM: Mus musculus

<400> SEQUENCE: 4

```
Met Gly Thr Gly Phe Ala Arg Gly Ala Arg Gly Thr Ala Ala Ser Gly
1               5                   10                  15

Pro Gly Gly Gly Phe Leu Phe Ala Trp Ile Leu Val Ser Phe Thr Cys
                20                  25                  30

His Leu Ala Ser Thr Gln Gly Ala Pro Glu Asp Val Asp Val Leu Gln
            35                  40                  45

Arg Leu Gly Leu Ser Trp Thr Lys Ala Gly Gly Arg Ser Pro Thr
    50                  55                  60

Pro Pro Gly Val Ile Pro Phe Pro Ser Gly Phe Ile Phe Thr Gln Arg
65                  70                  75                  80

Ala Lys Leu Gln Ala Pro Thr Ala Asn Val Leu Pro Thr Thr Leu Gly
                85                  90                  95

Arg Glu Leu Ala Leu Val Leu Ser Leu Cys Ser His Arg Val Asn His
            100                 105                 110

Ala Phe Leu Phe Ala Ile Arg Ser Arg Lys His Lys Leu Gln Leu Gly
        115                 120                 125

Leu Gln Phe Leu Pro Gly Arg Thr Ile Ile His Leu Gly Pro Arg Gln
    130                 135                 140

Ser Val Ala Phe Asp Leu Asp Val His Asp Gly Arg Trp His His Leu
145                 150                 155                 160

Ala Leu Glu Leu Arg Gly Arg Thr Val Thr Met Val Thr Ala Cys Gly
                165                 170                 175

Gln His Arg Val Pro Val Pro Leu Pro Ser Arg Arg Asp Ser Met Leu
            180                 185                 190
```

```
Asp Pro Gln Gly Ser Phe Leu Leu Gly Lys Val Asn Pro Arg Ala Val
            195                 200                 205

Gln Phe Glu Gly Ala Leu Cys Gln Phe Ser Ile His Pro Val Ala Gln
        210                 215                 220

Val Ala His Asn Tyr Cys Ala His Leu Arg Glu Arg Cys Arg Gln Val
225                 230                 235                 240

Asp Thr Tyr Ser Pro Gln Val Gly Thr Leu Phe Pro Trp Asp Ser Gly
            245                 250                 255

Pro Ala Phe Ala Leu His Pro Glu Pro Ala Leu Leu Gly Leu Gly Asn
        260                 265                 270

Leu Thr Arg Thr Pro Ala Thr Leu Gly Ala Arg Pro Val Ser Arg Ala
        275                 280                 285

Leu Ala Val Thr Leu Ala Pro Ala Met Pro Thr Lys Pro Leu Arg Thr
        290                 295                 300

Val His Pro Asp Val Ser Glu His Ser Ser Gln Thr Pro Leu Ser
305                 310                 315                 320

Pro Ala Lys Gln Ser Ala Arg Lys Thr Pro Ser Pro Ser Ser Ser Ala
            325                 330                 335

Ser Leu Ala Asn Ser Thr Arg Val Tyr Arg Pro Ala Ala Gln Pro
            340                 345                 350

Arg Gln Ile Thr Thr Thr Ser Pro Thr Lys Arg Ser Pro Thr Lys Pro
            355                 360                 365

Ser Val Ser Pro Leu Ser Val Thr Pro Met Lys Ser Pro His Ala Thr
            370                 375                 380

Gln Lys Thr Gly Val Pro Ser Phe Thr Lys Pro Val Pro Pro Thr Gln
385                 390                 395                 400

Lys Pro Ala Pro Phe Thr Ser Tyr Leu Ala Pro Ser Lys Ala Ser Ser
            405                 410                 415

Pro Thr Val Arg Pro Val Gln Lys Thr Phe Met Thr Pro Arg Pro Pro
            420                 425                 430

Val Pro Ser Pro Gln Pro Leu Arg Pro Thr Thr Gly Leu Ser Lys Lys
            435                 440                 445

Phe Thr Asn Pro Thr Val Ala Lys Ser Lys Ser Lys Thr Thr Ser Trp
450                 455                 460

Ala Ser Lys Pro Val Leu Ala Arg Ser Val Pro Lys Thr Leu Gln
465                 470                 475                 480

Gln Thr Val Leu Ser Gln Ser Pro Val Ser Tyr Leu Gly Ser Gln Thr
            485                 490                 495

Leu Ala Pro Ala Leu Pro Pro Leu Gly Val Gly Asn Pro Arg Thr Met
            500                 505                 510

Pro Pro Thr Arg Asp Ser Ala Leu Thr Pro Ala Gly Ser Lys Lys Phe
            515                 520                 525

Thr Gly Arg Glu Thr Ser Lys Lys Thr Arg Gln Lys Ser Ser Pro Arg
            530                 535                 540

Lys Pro Glu Pro Leu Ser Pro Gly Lys Ser Ala Arg Asp Ala Ser Pro
545                 550                 555                 560

Arg Asp Leu Thr Thr Lys Pro Ser Arg Pro Ser Thr Pro Ala Leu Val
            565                 570                 575

Leu Ala Pro Ala Tyr Leu Leu Ser Ser Ser Pro Gln Pro Thr Ser Ser
            580                 585                 590

Ser Phe Pro Phe Phe His Leu Leu Gly Pro Thr Pro Phe Pro Met Leu
            595                 600                 605

Met Gly Pro Pro Gly Ser Lys Gly Asp Cys Gly Leu Pro Gly Pro Pro
```

```
                610                 615                 620
Gly Leu Pro Gly Leu Pro Gly Ser Pro Gly Ala Arg Gly Pro Arg Gly
625                 630                 635                 640

Pro Pro Gly Pro Tyr Gly Asn Pro Gly Pro Pro Gly Pro Pro Gly Ala
                645                 650                 655

Lys Gly Gln Lys Gly Asp Pro Gly Leu Ser Pro Gly Gln Ala His Asp
                660                 665                 670

Gly Ala Lys Gly Asn Met Gly Leu Pro Gly Leu Ser Gly Asn Pro Gly
                675                 680                 685

Pro Leu Gly Arg Lys Gly His Lys Gly His Pro Gly Ala Ala Gly His
690                 695                 700

Pro Gly Glu Gln Gly Gln Pro Gly Pro Glu Gly Ser Pro Gly Ala Lys
705                 710                 715                 720

Gly Tyr Pro Gly Arg Gln Gly Phe Pro Gly Pro Val Gly Asp Pro Gly
                725                 730                 735

Pro Lys Gly Ser Arg Gly Tyr Ile Gly Leu Pro Gly Leu Phe Gly Leu
                740                 745                 750

Pro Gly Ser Asp Gly Glu Arg Gly Leu Pro Gly Val Pro Gly Lys Arg
                755                 760                 765

Gly Glu Met Gly Arg Pro Gly Phe Pro Gly Asp Phe Gly Glu Arg Gly
                770                 775                 780

Pro Pro Gly Leu Asp Gly Asn Pro Gly Glu Ile Gly Leu Pro Gly Pro
785                 790                 795                 800

Pro Gly Val Leu Gly Leu Ile Gly Asp Thr Gly Ala Leu Gly Pro Val
                805                 810                 815

Gly Tyr Pro Gly Pro Lys Gly Met Lys Gly Leu Met Gly Gly Val Gly
                820                 825                 830

Glu Pro Gly Leu Lys Gly Asp Lys Gly Glu Gln Gly Val Pro Gly Val
                835                 840                 845

Ser Gly Asp Pro Gly Phe Gln Gly Asp Lys Gly Ser His Gly Leu Pro
                850                 855                 860

Gly Leu Pro Gly Gly Arg Gly Lys Pro Gly Pro Leu Gly Lys Ala Gly
865                 870                 875                 880

Asp Lys Gly Ser Leu Gly Phe Pro Gly Pro Pro Gly Pro Glu Gly Phe
                885                 890                 895

Pro Gly Asp Ile Gly Pro Pro Gly Asp Asn Gly Pro Glu Gly Met Lys
                900                 905                 910

Gly Lys Pro Gly Ala Arg Gly Leu Pro Gly Pro Pro Gly Gln Leu Gly
                915                 920                 925

Pro Glu Gly Asp Glu Gly Pro Met Gly Pro Pro Gly Val Pro Gly Leu
930                 935                 940

Glu Gly Gln Pro Gly Arg Lys Gly Phe Pro Gly Arg Pro Gly Leu Asp
945                 950                 955                 960

Gly Ser Lys Gly Glu Pro Gly Asp Pro Gly Arg Pro Gly Pro Val Gly
                965                 970                 975

Glu Gln Gly Leu Met Gly Phe Ile Gly Leu Val Gly Glu Pro Gly Ile
                980                 985                 990

Val Gly Glu Lys Gly Asp Arg Gly Val Met Gly Pro Pro Gly Ala Pro
                995                 1000                1005

Gly Pro Lys Gly Ser Met Gly His Pro Gly Thr Pro Gly Gly Ile
                1010                1015                1020

Gly Asn Pro Gly Glu Pro Gly Pro Trp Gly Pro Pro Gly Ser Arg
                1025                1030                1035
```

-continued

Gly Leu Pro Gly Met Arg Gly Ala Lys Gly His Arg Gly Pro Arg
    1040            1045            1050

Gly Pro Asp Gly Pro Ala Gly Glu Gln Gly Ser Lys Gly Leu Lys
    1055            1060            1065

Gly Arg Val Gly Pro Arg Gly Arg Pro Gly Gln Pro Gly Gln Gln
    1070            1075            1080

Gly Ala Ala Gly Glu Arg Gly His Ser Gly Ala Lys Gly Phe Leu
    1085            1090            1095

Gly Ile Pro Gly Pro Ser Gly Pro Pro Gly Ala Lys Gly Leu Pro
    1100            1105            1110

Gly Glu Pro Gly Ser Gln Gly Pro Gln Gly Pro Val Gly Pro Pro
    1115            1120            1125

Gly Glu Met Gly Pro Lys Gly Pro Pro Gly Ala Val Gly Glu Pro
    1130            1135            1140

Gly Leu Pro Gly Asp Ser Gly Met Lys Gly Asp Leu Gly Pro Leu
    1145            1150            1155

Gly Pro Pro Gly Glu Gln Gly Leu Ile Gly Gln Arg Gly Glu Pro
    1160            1165            1170

Gly Leu Glu Gly Asp His Gly Pro Val Gly Pro Asp Gly Leu Lys
    1175            1180            1185

Gly Asp Arg Gly Asp Pro Gly Pro Asp Gly Glu His Gly Glu Lys
    1190            1195            1200

Gly Gln Glu Gly Leu Lys Gly Glu Asp Gly Ser Pro Gly Pro Pro
    1205            1210            1215

Gly Ile Thr Gly Val Pro Gly Arg Glu Gly Lys Pro Gly Lys Gln
    1220            1225            1230

Gly Glu Lys Gly Gln Arg Gly Ala Lys Gly Ala Lys Gly His Gln
    1235            1240            1245

Gly Tyr Leu Gly Glu Met Gly Ile Pro Gly Glu Pro Gly Pro Pro
    1250            1255            1260

Gly Thr Pro Gly Pro Lys Gly Ser Arg Gly Thr Leu Gly Pro Thr
    1265            1270            1275

Gly Ala Pro Gly Arg Met Gly Ala Gln Gly Glu Pro Gly Leu Ala
    1280            1285            1290

Gly Tyr Asn Gly His Lys Gly Ile Thr Gly Pro Leu Gly Pro Pro
    1295            1300            1305

Gly Pro Lys Gly Glu Lys Gly Asp Gln Gly Glu Asp Gly Lys Thr
    1310            1315            1320

Glu Gly Pro Pro Gly Pro Pro Gly Asp Arg Gly Pro Val Gly Asp
    1325            1330            1335

Arg Gly Asp Arg Gly Glu Pro Gly Asp Pro Gly Tyr Pro Gly Gln
    1340            1345            1350

Glu Gly Val Gln Gly Leu Arg Gly Glu Pro Gly Gln Gln Gly Gln
    1355            1360            1365

Pro Gly His Pro Gly Pro Arg Gly Arg Pro Gly Pro Lys Gly Ser
    1370            1375            1380

Lys Gly Glu Glu Gly Pro Lys Gly Lys Pro Gly Lys Ala Gly Pro
    1385            1390            1395

Ser Gly Arg Arg Gly Thr Gln Gly Leu Gln Gly Leu Pro Gly Pro
    1400            1405            1410

Arg Gly Val Val Gly Arg Gln Gly Pro Glu Gly Thr Ala Gly Ser
    1415            1420            1425

```
Asp Gly Ile Pro Gly Arg Asp Gly Arg Pro Gly Tyr Gln Gly Asp
    1430            1435            1440

Gln Gly Asn Asp Gly Asp Pro Gly Pro Val Gly Pro Ala Gly Arg
    1445            1450            1455

Arg Gly Asn Pro Gly Val Ala Gly Leu Pro Gly Ala Gln Gly Pro
    1460            1465            1470

Pro Gly Phe Lys Gly Glu Ser Gly Leu Pro Gly Gln Leu Gly Pro
    1475            1480            1485

Pro Gly Lys Arg Gly Thr Glu Gly Gly Thr Gly Leu Pro Gly Asn
    1490            1495            1500

Gln Gly Glu Pro Gly Ser Lys Gly Gln Pro Gly Asp Ser Gly Glu
    1505            1510            1515

Met Gly Phe Pro Gly Val Ala Gly Leu Phe Gly Pro Lys Gly Pro
    1520            1525            1530

Pro Gly Asp Ile Gly Phe Lys Gly Ile Gln Gly Pro Arg Gly Pro
    1535            1540            1545

Pro Gly Leu Met Gly Lys Glu Gly Ile Ile Gly Pro Pro Gly Met
    1550            1555            1560

Leu Gly Pro Ser Gly Leu Pro Gly Pro Lys Gly Asp Arg Gly Ser
    1565            1570            1575

Arg Gly Asp Leu Gly Leu Gln Gly Pro Arg Gly Pro Pro Gly Pro
    1580            1585            1590

Arg Gly Arg Pro Gly Pro Pro Gly Pro Pro Trp His Pro Ile Gln
    1595            1600            1605

Phe Gln Gln Asp Asp Leu Gly Ala Ala Phe Gln Thr Trp Met Asp
    1610            1615            1620

Ala Gln Gly Ala Val Arg Ser Glu Gly Tyr Ser Tyr Pro Asp Gln
    1625            1630            1635

Leu Ala Leu Asp Gln Gly Gly Glu Ile Phe Lys Thr Leu His Tyr
    1640            1645            1650

Leu Ser Asn Leu Ile Gln Ser Ile Lys Thr Pro Leu Gly Thr Lys
    1655            1660            1665

Glu Asn Pro Ala Arg Val Cys Arg Asp Leu Met Asp Cys Glu Gln
    1670            1675            1680

Arg Met Ala Asp Gly Thr Tyr Trp Val Asp Pro Asn Leu Gly Cys
    1685            1690            1695

Ser Ser Asp Thr Ile Glu Val Ser Cys Asn Phe Thr Gln Gly Gly
    1700            1705            1710

Gln Thr Cys Leu Lys Pro Ile Thr Ala Ser Lys Ala Glu Phe Ala
    1715            1720            1725

Val Ser Arg Val Gln Met Asn Phe Leu His Leu Leu Ser Ser Glu
    1730            1735            1740

Gly Thr Gln His Ile Thr Ile His Cys Leu Asn Met Thr Val Trp
    1745            1750            1755

Gln Glu Gly Pro Gly Arg Ser Ser Ala Arg Gln Ala Val Arg Phe
    1760            1765            1770

Arg Ala Trp Asn Gly Gln Val Phe Glu Ala Gly Gly Gln Phe Arg
    1775            1780            1785

Pro Glu Val Ser Met Asp Gly Cys Lys Val His Asp Gly Arg Trp
    1790            1795            1800

His Gln Thr Leu Phe Thr Phe Arg Thr Gln Asp Pro Gln Gln Leu
    1805            1810            1815

Pro Ile Val Ser Val Asp Asn Leu Pro Pro Val Ser Ser Gly Lys
```

Gln Tyr Arg Leu Glu Val Gly Pro Ala Cys Phe Leu
　　　1835　　　　　　1840　　　　　　1845

<210> SEQ ID NO 5
<211> LENGTH: 5568
<212> TYPE: DNA
<213> ORGANISM: Rattus norvegicus

<400> SEQUENCE: 5

| | | | | | |
|---|---|---|---|---|---|
| atgggcctgg | cgcgggcgac | cgcggggctg | ggccgtgctg | tgccgcctgc | tccggcgctc | 60 |
| ctgggcgcag | gctgcgctg | gggggggattt | ctcttcgcct | ggatcttggt | ctcattttcc | 120 |
| tgtcatctgg | cctccaccca | aggagctcct | gaagatgtgg | atgtcctcca | gcggctgggc | 180 |
| ctcagctgga | cgaaagctgg | gggtggccgg | agccccgcac | ccctggtgt | cattcctttc | 240 |
| ccatctggct | tcatcttcac | acagcgggcc | aagctgcagg | ccctactac | caatgtcctt | 300 |
| cccaccaccc | tggggcggga | gctggcattg | tgttgagcc | tctgttcgca | ccgtgtgaac | 360 |
| catgccttcc | tcttcgccat | ccgcagcagg | aaacacaggc | tgcagctggg | tctgcagttc | 420 |
| ctccccggca | ggactctcgt | ccacctggga | cctcggcaat | ctgtggcctt | cgacttggat | 480 |
| gtgcatgatg | ggcgctggca | ccacctggcc | ctagagttgc | gtggtcgcac | ggtcacattg | 540 |
| gtgacagcct | gtgggcagca | cagggtacct | gttccgctgc | cttcccgtag | ggactccatg | 600 |
| cttgaccccc | agggctcctt | tctcttgggg | aagatgaacc | cccgagctgt | ccagtttgaa | 660 |
| ggtgcactct | gtcagttcag | catccatccc | gtggcgcagg | tcgctcacaa | ttactgtgcc | 720 |
| cacctgagag | aacggtgccg | acaggtggac | acgtatggtc | cccaggtggg | agccctcttt | 780 |
| ccctgggact | ctggcccagc | ctttgctttg | catcctgaac | cagccttgct | tggtctgggg | 840 |
| aacctgacca | gaaacccagc | aaccctaggg | tccaggccta | aagcagggg | actcatggtg | 900 |
| actatggctc | ctgccgtgcc | caccaagccc | ctaaggatgg | tccaccaaga | tgtctccaaa | 960 |
| ctcggctctt | ctcagacccc | attggtccct | gccaaacagt | cagccagaaa | acaccttcc | 1020 |
| cccttccctt | cagctgctct | ggctaattcc | accagggttt | ttcactcagc | tcctgcccag | 1080 |
| ccacgacaaa | tcacagctac | tagccccacc | aaacgtcccc | cgaccaagcc | ttctgttcct | 1140 |
| tcccttcag | ttaccccat | gaaagtccc | caggcaatcc | agaaagcagg | taccccttca | 1200 |
| ttctcaaggc | ccattccaac | cacccagaag | ccaacacccc | tcacctccca | cccatcaccc | 1260 |
| tccaaagtct | ctagtgccac | tgtgaggcct | gtccagaaga | ctttcatgac | accccaacct | 1320 |
| ccaaccctga | gtcccaagc | cctgcaccct | attactggct | tacctaagaa | gttcactatc | 1380 |
| cccacagtag | caaaacctca | gtccaagatg | accagttggg | ccagcaagcc | agtcttggcc | 1440 |
| cgcaccaatg | tccctaaggc | tcttgagcaa | actgttgtgg | cccagtcctc | tgtttcctat | 1500 |
| ctgggctctc | agacactggc | tacagccctc | cctcctctgg | gtgttggaaa | ttctagaatg | 1560 |
| atgccttcca | cacgtgactc | tacttcaact | cctgctggaa | gcaagaaaat | cacaggattg | 1620 |
| gaagcttcca | agaaaaccag | acataagagc | agccccgga | agcccatacc | tctcagctct | 1680 |
| gggaagacag | ccagggatgc | ttcaccaaga | gacctgacaa | ccaagcctag | ccagctgtcc | 1740 |
| actccagccc | tggtccttgc | cccagcccac | ctccgtgtcct | ccagccccca | gcccaccagc | 1800 |
| agcagctttt | ctttcttcca | cctgccggaa | cctacacctt | tcctgatgct | gatgggcct | 1860 |
| cctggctcca | agggagactg | tggcttgccg | ggcctctg | ggcttccagg | attacctgga | 1920 |
| tctccgggtc | cacgaggtcc | tcggggtcct | cctgggcat | ttgggaaccc | aggtctacct | 1980 |

```
ggacctcctg gagccaaagg acagaaaggg gacccgggac tctcaccagg acaggctcac    2040 gatgggcaa  agggcaacat gggcttgcct gggctcgccg gaaatccagg acccatggga    2100
cggaagggac acaagggcca ccctggagcg gcagggcacc ctggagaaca ggggcagcca    2160
ggacctgagg gcagtccagg ggccaaaggt taccctggca ggcagggggtt ccctggacct   2220 gtaggagacc ctggccccaa aggcagcagg ggttacattg ggcttccggg gctctttggc    2280
ctgccagggt cggatggaga gcggggtctc cccggcattc ctgcaagag  gggcgagatg    2340 ggtaggccgg gcttccctgg agactttggg gaaagaggtc cccctggact tgatgggaac    2400
cctggggaaa ttggcctgcc aggaccacca ggagtgctcg ggctccttgg tgacatggga    2460
gcattaggtc cagttggcta cccgggacca aaaggcatga agggactgat gggcggcgtg    2520
ggggagcccg gactgaaagg tgataagggg gaacaagggg tgccaggtgt atcgggagat    2580
cctggcttcc aaggagacaa ggggagtcat ggcttgccag ggttcccagg tgcccggggg    2640
aagccagggc ctatgggcaa agctggggac aaaggctcac ttgggcttcc tggacctcct   2700
ggtcctgagg gtttcccagg agacattggc cccccagggg acaatggccc tgaaggcatg    2760
aagggtaagc ctggagcccg aggcctacct ggacctcctg gcagctggg  gcctgaggga    2820 gatgaaggac ccatggggcc accaggagtc ccaggcttgg agggtcaacc tggaaggaag    2880
gggttcccgg ggaggcctgg cctggacggc tcgaagggg  aaccagggga tcctggacgg    2940
ccagggcctg tgggtgaaca ggggcttatg ggatttgttg gtctggttgg agagcctgga    3000
attgttgggg agaagggaga ccgtggagtg atgggacccc caggggcacc tggacccaag    3060
gggtcgatgg gccatcctgg aacacctggt ggtgttgggg accctggaga gcctggaccc    3120
tggggccctc caggatctcg aggactgcca ggcatgaggg gagccaaggg gcaccggggc    3180
cctcgaggac ctgatggacc agctggggag caggggtcca agggcctgaa gggtcgtgta    3240
gggcctcggg gcagacctgg ccagccagga cagcagggtg cagctggcga gcgaggccac    3300
tcaggtgcaa aaggcttcct tggcattcct ggtcccctcag gccctccagg tgccaagggc    3360
ctcccaggag aaccgggctc tcagggacct caggggccag ttggtcctcc aggagagatg    3420
ggacccaagg ggcgcctgg  tgcagtggga gaacctggcc ttcctgggga ctccggtatg    3480
aagggtgacc ttggacctct gggccctcct ggggaacaag ggctcattgg caacgggga    3540 gagccaggcc tcgagggaga ccttggccca gtggggccag atgggctgaa ggggacagg    3600 ggtgacccag gtcctgatgg tgaacatggt gaaaagggtc aggaaggact gaaaggagag    3660
gaggggctcc ctgggccccc aggcatcact ggtgtccggg gtcgtgaagg gaagcctggc    3720
agtcagggtg agaagggcca gaggggagct aagggtgcca agggctacca aggacagctg    3780
ggagagatgg gcatccctgg agaccctggc cccctggca  ccccaggtcc taaagggtcc    3840
cggggcaccc taggaccaat gggtgctcca ggacggatgg gagcccaagg agaaccagga    3900
ttggctggtt ataatgggca taaaggcatc acgggacctc tcgggcctcc cgggcccaaa    3960
ggcgagaagg ggaacaggg  cgaggatggc aagactgagg gggcccccgg gccaccagga    4020
gagcggggtc ctgtgggtga tcgaggagac cgtggggagc caggcgaccc tggataccct    4080
ggtcaagagg tgttcaagg  cctccgtgga gaaccaggcc agcagggcca gcccgggcat    4140
ccaggacccc ggggacgccc aggacccaaa ggatcaaaag gcgaagaggg cccaaaggga    4200
aagccaggca aggcggggc  atcaggccgg agggggaccc aggggcttca agggctgcca    4260
gggcgagaga gtgtagtagg gagacagggc cctgagggca tggctggaca agatgggaat    4320
cctggcaggg acggtcggcc aggatatcag ggagagcagg gaaatgatgg ggaccctggc    4380
```

```
cccgtgggcc ctgctgggag aagagggaat ccaggtgtgg ctggcttgcc tggagcacag    4440
gggcctccag gattcaaggg tgaaagtggg ttacctgggc aactgggtcc ccctggaaaa    4500
cgagggacag aaggtggaac ggggcttcct gggaaccagg gggagccagg atccaaaggc    4560
cagccgggtg actctggcga gatgggcttc caggagtgg ctggcctctt tggacccaag     4620
ggtccccctg gagacattgg cttcaaaggc atccaaggcc ctcggggtcc tcctggcttg    4680
atgggaaagg aaggtatcat tgggcccccc ggaatgctgg gaccttctgg actcccgggt    4740
cccaaaggtg acagaggcag ccgagggac tggggactgc aaggcccaag gggtcctcct     4800
ggtccgaggg ggcggccagg tccaccgggc cctccttggc atcctgtcca gtttcaacaa    4860
gatgaccttg aggcagcttt ccaaacgtgg atggatgctc acggagcagt cagattggag    4920 cagggggtaca gctatccgga ccagctgatg ctagaccagg gaggggagat cttcaaaacc    4980
ttacactacc tcagcaacct catccagagc attaagacgc ccttgggcac caaggagaac    5040
ccagcccggg tctgccggga cctcatggac tgcgaacaga gatggcgga tggtatctac     5100 tgggtggacc ccaacctcgg ctgctcctct gataccatcg aagtctcctg caactttaca    5160
catggtgggc agacttgcct gaagcctatc acggcctcca aggcagagtt tgctgttagt    5220
cgggtccaga tgaatttctt gcacctgctc agctctgagg ggacacagca catcacaatc    5280
cactgcctga acatgacggt gtggcaggag ggacctgcac gcccctctgc caggcaagct    5340
gtgcgcttcc gtgcctggaa cggacaggtc tttgaagctg ggggtcaatt caggccagag    5400
gtgtctatgg atggctgcaa ggtccatgat ggccgctggc atcagacact attcaccttc    5460
cggacccagg accccagca gctgcccatt gtcagtgtgg acaaccttcc acctgtctcg     5520
tcagggaagc agtaccgcct ggaagttgga cctgcatgct tcctctga                 5568
```

<210> SEQ ID NO 6
<211> LENGTH: 1855
<212> TYPE: PRT
<213> ORGANISM: Rattus norvegicus

<400> SEQUENCE: 6

```
Met Gly Leu Ala Arg Ala Thr Ala Gly Leu Gly Pro Cys Cys Pro Pro
1               5                   10                  15

Ala Pro Ala Leu Leu Gly Ala Gly Leu Arg Trp Gly Gly Phe Leu Phe
                20                  25                  30

Ala Trp Ile Leu Val Ser Phe Ser Cys His Leu Ala Ser Thr Gln Gly
            35                  40                  45

Ala Pro Glu Asp Val Asp Val Leu Gln Arg Leu Gly Leu Ser Trp Thr
        50                  55                  60

Lys Ala Gly Gly Arg Ser Pro Ala Pro Gly Val Ile Pro Phe
65                  70                  75                  80

Pro Ser Gly Phe Ile Phe Thr Gln Arg Ala Lys Leu Gln Ala Pro Thr
                85                  90                  95

Thr Asn Val Leu Pro Thr Thr Leu Gly Arg Glu Leu Ala Leu Val Leu
                100                 105                 110

Ser Leu Cys Ser His Arg Val Asn His Ala Phe Leu Phe Ala Ile Arg
            115                 120                 125

Ser Arg Lys His Arg Leu Gln Leu Gly Leu Gln Phe Leu Pro Gly Arg
        130                 135                 140

Thr Leu Val His Leu Gly Pro Arg Gln Ser Val Ala Phe Asp Leu Asp
145                 150                 155                 160
```

-continued

```
Val His Asp Gly Arg Trp His His Leu Ala Leu Glu Leu Arg Gly Arg
            165                 170                 175

Thr Val Thr Leu Val Thr Ala Cys Gly Gln His Arg Val Pro Val Pro
        180                 185                 190

Leu Pro Ser Arg Arg Asp Ser Met Leu Asp Pro Gln Gly Ser Phe Leu
    195                 200                 205

Leu Gly Lys Met Asn Pro Arg Ala Val Gln Phe Glu Gly Ala Leu Cys
210                 215                 220

Gln Phe Ser Ile His Pro Val Ala Gln Val Ala His Asn Tyr Cys Ala
225                 230                 235                 240

His Leu Arg Glu Arg Cys Arg Gln Val Asp Thr Tyr Gly Pro Gln Val
                245                 250                 255

Gly Ala Leu Phe Pro Trp Asp Ser Gly Pro Ala Phe Ala Leu His Pro
            260                 265                 270

Glu Pro Ala Leu Leu Gly Leu Gly Asn Leu Thr Arg Asn Pro Ala Thr
        275                 280                 285

Leu Gly Ser Arg Pro Ile Ser Arg Gly Leu Met Val Thr Met Ala Pro
    290                 295                 300

Ala Val Pro Thr Lys Pro Leu Arg Met Val His Gln Asp Val Ser Lys
305                 310                 315                 320

Leu Gly Ser Ser Gln Thr Pro Leu Val Pro Ala Lys Gln Ser Ala Arg
                325                 330                 335

Lys Thr Pro Ser Pro Phe Pro Ser Ala Ala Leu Ala Asn Ser Thr Arg
            340                 345                 350

Val Phe His Ser Ala Pro Ala Gln Pro Arg Gln Ile Thr Ala Thr Ser
        355                 360                 365

Pro Thr Lys Arg Pro Pro Thr Lys Pro Ser Val Ser Ser Leu Ser Val
    370                 375                 380

Thr Pro Met Lys Ser Pro Gln Ala Ile Gln Lys Ala Gly Thr Pro Ser
385                 390                 395                 400

Phe Ser Arg Pro Ile Pro Thr Thr Gln Lys Pro Thr Pro Leu Thr Ser
                405                 410                 415

His Pro Ser Pro Ser Lys Val Ser Ser Ala Thr Val Arg Pro Val Gln
            420                 425                 430

Lys Thr Phe Met Thr Pro Gln Pro Pro Thr Leu Ser Pro Gln Ala Leu
        435                 440                 445

His Pro Ile Thr Gly Leu Pro Lys Lys Phe Thr Ile Pro Thr Val Ala
    450                 455                 460

Lys Pro Gln Ser Lys Met Thr Ser Trp Ala Ser Lys Pro Val Leu Ala
465                 470                 475                 480

Arg Thr Asn Val Pro Lys Ala Leu Glu Gln Thr Val Val Ala Gln Ser
                485                 490                 495

Ser Val Ser Tyr Leu Gly Ser Gln Thr Leu Ala Thr Ala Leu Pro Pro
            500                 505                 510

Leu Gly Val Gly Asn Ser Arg Met Met Pro Ser Thr Arg Asp Ser Thr
        515                 520                 525

Ser Thr Pro Ala Gly Ser Lys Lys Ile Thr Gly Leu Glu Ala Ser Lys
    530                 535                 540

Lys Thr Arg His Lys Ser Ser Pro Arg Lys Pro Ile Pro Leu Ser Ser
545                 550                 555                 560

Gly Lys Thr Ala Arg Asp Ala Ser Pro Arg Asp Leu Thr Thr Lys Pro
                565                 570                 575

Ser Gln Leu Ser Thr Pro Ala Leu Val Leu Ala Pro Ala His Leu Leu
```

-continued

```
            580                 585                 590
Ser Ser Ser Pro Gln Pro Thr Ser Ser Phe Ser Phe His Leu
            595                 600             605
Pro Glu Pro Thr Pro Phe Leu Met Leu Met Gly Pro Pro Gly Ser Lys
610                     615                 620
Gly Asp Cys Gly Leu Pro Gly Pro Pro Gly Leu Pro Gly Leu Pro Gly
625                 630                 635                 640
Ser Pro Gly Pro Arg Gly Pro Arg Gly Pro Pro Gly Pro Phe Gly Asn
                645                 650                 655
Pro Gly Leu Pro Gly Pro Pro Gly Ala Lys Gly Gln Lys Gly Asp Pro
            660                 665                 670
Gly Leu Ser Pro Gly Gln Ala His Asp Gly Ala Lys Gly Asn Met Gly
            675                 680                 685
Leu Pro Gly Leu Ala Gly Asn Pro Gly Pro Met Gly Arg Lys Gly His
            690                 695                 700
Lys Gly His Pro Gly Ala Ala Gly His Pro Gly Glu Gln Gly Gln Pro
705                 710                 715                 720
Gly Pro Glu Gly Ser Pro Gly Ala Lys Gly Tyr Pro Gly Arg Gln Gly
                725                 730                 735
Phe Pro Gly Pro Val Gly Asp Pro Gly Pro Lys Gly Ser Arg Gly Tyr
                740                 745                 750
Ile Gly Leu Pro Gly Leu Phe Gly Leu Pro Gly Ser Asp Gly Glu Arg
            755                 760                 765
Gly Leu Pro Gly Ile Pro Gly Lys Arg Gly Glu Met Gly Arg Pro Gly
            770                 775                 780
Phe Pro Gly Asp Phe Gly Glu Arg Gly Pro Pro Gly Leu Asp Gly Asn
785                 790                 795                 800
Pro Gly Glu Ile Gly Leu Pro Gly Pro Gly Val Leu Gly Leu Leu
                805                 810                 815
Gly Asp Met Gly Ala Leu Gly Pro Val Gly Tyr Pro Gly Pro Lys Gly
                820                 825                 830
Met Lys Gly Leu Met Gly Gly Val Gly Glu Pro Gly Leu Lys Gly Asp
            835                 840                 845
Lys Gly Glu Gln Gly Val Pro Gly Val Ser Gly Asp Pro Gly Phe Gln
            850                 855                 860
Gly Asp Lys Gly Ser His Gly Leu Pro Gly Phe Pro Gly Ala Arg Gly
865                 870                 875                 880
Lys Pro Gly Pro Met Gly Lys Ala Gly Asp Lys Gly Ser Leu Gly Leu
                885                 890                 895
Pro Gly Pro Pro Gly Pro Glu Gly Phe Pro Gly Asp Ile Gly Pro Pro
            900                 905                 910
Gly Asp Asn Gly Pro Glu Gly Met Lys Gly Lys Pro Gly Ala Arg Gly
            915                 920                 925
Leu Pro Gly Pro Gly Gln Leu Gly Pro Glu Gly Asp Glu Gly Pro
            930                 935                 940
Met Gly Pro Pro Gly Val Pro Gly Leu Glu Gly Gln Pro Gly Arg Lys
945                 950                 955                 960
Gly Phe Pro Gly Arg Pro Gly Leu Asp Gly Ser Lys Gly Glu Pro Gly
                965                 970                 975
Asp Pro Gly Arg Pro Gly Pro Val Gly Glu Gln Gly Leu Met Gly Phe
            980                 985                 990
Val Gly Leu Val Gly Glu Pro Gly  Ile Val Gly Glu Lys  Gly Asp Arg
            995                     1000                1005
```

```
Gly Val Met Gly Pro Pro Gly Ala Pro Gly Pro Lys Gly Ser Met
1010            1015            1020

Gly His Pro Gly Thr Pro Gly Val Gly Asp Pro Gly Glu Pro
1025            1030            1035

Gly Pro Trp Gly Pro Gly Ser Arg Gly Leu Pro Gly Met Arg
1040            1045            1050

Gly Ala Lys Gly His Arg Gly Pro Arg Gly Pro Asp Gly Pro Ala
1055            1060            1065

Gly Glu Gln Gly Ser Lys Gly Leu Lys Gly Arg Val Gly Pro Arg
1070            1075            1080

Gly Arg Pro Gly Gln Pro Gly Gln Gln Gly Ala Ala Gly Glu Arg
1085            1090            1095

Gly His Ser Gly Ala Lys Gly Phe Leu Gly Ile Pro Gly Pro Ser
1100            1105            1110

Gly Pro Pro Gly Ala Lys Gly Leu Pro Gly Glu Pro Gly Ser Gln
1115            1120            1125

Gly Pro Gln Gly Pro Val Gly Pro Pro Gly Glu Met Gly Pro Lys
1130            1135            1140

Gly Pro Pro Gly Ala Val Gly Glu Pro Gly Leu Pro Gly Asp Ser
1145            1150            1155

Gly Met Lys Gly Asp Leu Gly Pro Leu Gly Pro Pro Gly Glu Gln
1160            1165            1170

Gly Leu Ile Gly Gln Arg Gly Glu Pro Gly Leu Glu Gly Asp Leu
1175            1180            1185

Gly Pro Val Gly Pro Asp Gly Leu Lys Gly Asp Arg Gly Asp Pro
1190            1195            1200

Gly Pro Asp Gly Glu His Gly Glu Lys Gly Gln Glu Gly Leu Lys
1205            1210            1215

Gly Glu Glu Gly Leu Pro Gly Pro Pro Gly Ile Thr Gly Val Arg
1220            1225            1230

Gly Arg Glu Gly Lys Pro Gly Ser Gln Gly Glu Lys Gly Gln Arg
1235            1240            1245

Gly Ala Lys Gly Ala Lys Gly Tyr Gln Gly Gln Leu Gly Glu Met
1250            1255            1260

Gly Ile Pro Gly Asp Pro Gly Pro Pro Gly Thr Pro Gly Pro Lys
1265            1270            1275

Gly Ser Arg Gly Thr Leu Gly Pro Met Gly Ala Pro Gly Arg Met
1280            1285            1290

Gly Ala Gln Gly Glu Pro Gly Leu Ala Gly Tyr Asn Gly His Lys
1295            1300            1305

Gly Ile Thr Gly Pro Leu Gly Pro Pro Gly Pro Lys Gly Glu Lys
1310            1315            1320

Gly Glu Gln Gly Glu Asp Gly Lys Thr Glu Gly Ala Pro Gly Pro
1325            1330            1335

Pro Gly Glu Arg Gly Pro Val Gly Asp Arg Gly Asp Arg Gly Glu
1340            1345            1350

Pro Gly Asp Pro Gly Tyr Pro Gly Gln Glu Gly Val Gln Gly Leu
1355            1360            1365

Arg Gly Glu Pro Gly Gln Gln Gly Gln Pro Gly His Pro Gly Pro
1370            1375            1380

Arg Gly Arg Pro Gly Pro Lys Gly Ser Lys Gly Glu Glu Gly Pro
1385            1390            1395
```

```
Lys Gly Lys Pro Gly Lys Ala Gly Ser Gly Arg Arg Gly Thr
    1400            1405            1410

Gln Gly Leu Gln Gly Leu Pro Gly Pro Arg Gly Val Val Gly Arg
    1415            1420            1425

Gln Gly Pro Glu Gly Met Ala Gly Gln Asp Gly Asn Pro Gly Arg
    1430            1435            1440

Asp Gly Arg Pro Gly Tyr Gln Gly Glu Gln Gly Asn Asp Gly Asp
    1445            1450            1455

Pro Gly Pro Val Gly Pro Ala Gly Arg Arg Gly Asn Pro Gly Val
    1460            1465            1470

Ala Gly Leu Pro Gly Ala Gln Gly Pro Pro Gly Phe Lys Gly Glu
    1475            1480            1485

Ser Gly Leu Pro Gly Gln Leu Gly Pro Pro Gly Lys Arg Gly Thr
    1490            1495            1500

Glu Gly Gly Thr Gly Leu Pro Gly Asn Gln Gly Glu Pro Gly Ser
    1505            1510            1515

Lys Gly Gln Pro Gly Asp Ser Gly Glu Met Gly Phe Pro Gly Val
    1520            1525            1530

Ala Gly Leu Phe Gly Pro Lys Gly Pro Pro Gly Asp Ile Gly Phe
    1535            1540            1545

Lys Gly Ile Gln Gly Pro Arg Gly Pro Pro Gly Leu Met Gly Lys
    1550            1555            1560

Glu Gly Ile Ile Gly Pro Pro Gly Met Leu Gly Pro Ser Gly Leu
    1565            1570            1575

Pro Gly Pro Lys Gly Asp Arg Gly Ser Arg Gly Asp Trp Gly Leu
    1580            1585            1590

Gln Gly Pro Arg Gly Pro Pro Gly Pro Arg Gly Arg Pro Gly Pro
    1595            1600            1605

Pro Gly Pro Pro Trp His Pro Val Gln Phe Gln Gln Asp Asp Leu
    1610            1615            1620

Glu Ala Ala Phe Gln Thr Trp Met Asp Ala His Gly Ala Val Arg
    1625            1630            1635

Leu Glu Gln Gly Tyr Ser Tyr Pro Asp Gln Leu Met Leu Asp Gln
    1640            1645            1650

Gly Gly Glu Ile Phe Lys Thr Leu His Tyr Leu Ser Asn Leu Ile
    1655            1660            1665

Gln Ser Ile Lys Thr Pro Leu Gly Thr Lys Glu Asn Pro Ala Arg
    1670            1675            1680

Val Cys Arg Asp Leu Met Asp Cys Glu Gln Lys Met Ala Asp Gly
    1685            1690            1695

Ile Tyr Trp Val Asp Pro Asn Leu Gly Cys Ser Ser Asp Thr Ile
    1700            1705            1710

Glu Val Ser Cys Asn Phe Thr His Gly Gly Gln Thr Cys Leu Lys
    1715            1720            1725

Pro Ile Thr Ala Ser Lys Ala Glu Phe Ala Val Ser Arg Val Gln
    1730            1735            1740

Met Asn Phe Leu His Leu Leu Ser Ser Glu Gly Thr Gln His Ile
    1745            1750            1755

Thr Ile His Cys Leu Asn Met Thr Val Trp Gln Glu Gly Pro Ala
    1760            1765            1770

Arg Pro Ser Ala Arg Gln Ala Val Arg Phe Arg Ala Trp Asn Gly
    1775            1780            1785

Gln Val Phe Glu Ala Gly Gly Gln Phe Arg Pro Glu Val Ser Met
```

-continued

| | 1790 | | | | 1795 | | | | 1800 | | | |
|---|---|---|---|---|---|---|---|---|---|---|---|---|
| Asp | Gly | Cys | Lys | Val | His | Asp | Gly | Arg | Trp | His | Gln | Thr | Leu | Phe |
| | 1805 | | | | | 1810 | | | | 1815 | | |
| Thr | Phe | Arg | Thr | Gln | Asp | Pro | Gln | Gln | Leu | Pro | Ile | Val | Ser | Val |
| | 1820 | | | | | 1825 | | | | 1830 | | |
| Asp | Asn | Leu | Pro | Pro | Val | Ser | Ser | Gly | Lys | Gln | Tyr | Arg | Leu | Glu |
| | 1835 | | | | | 1840 | | | | 1845 | | |
| Val | Gly | Pro | Ala | Cys | Phe | Leu |
| | 1850 | | | | | 1855 |